United States Patent
Picher Serantes et al.

(10) Patent No.: US 11,920,189 B2
(45) Date of Patent: Mar. 5, 2024

(54) METHODS AND KITS FOR AMPLIFICATION OF DOUBLE STRANDED DNA

(71) Applicant: 4BASEBIO SL, Madrid (ES)

(72) Inventors: Ángel Joaquin Picher Serantes, Madrid (ES); Bettina Budeus, Mühlheim (DE)

(73) Assignee: 4BASEBIO SL, Madrid (ES)

( * ) Notice: Subject to any disclaimer, the term of this patent is extended or adjusted under 35 U.S.C. 154(b) by 517 days.

(21) Appl. No.: 16/763,921

(22) PCT Filed: Nov. 14, 2018

(86) PCT No.: PCT/EP2018/081219
§ 371 (c)(1),
(2) Date: May 13, 2020

(87) PCT Pub. No.: WO2019/101596
PCT Pub. Date: May 31, 2019

(65) Prior Publication Data
US 2020/0362403 A1 Nov. 19, 2020

Related U.S. Application Data

(60) Provisional application No. 62/589,074, filed on Nov. 21, 2017.

(51) Int. Cl.
*C12Q 1/6855* (2018.01)
(52) U.S. Cl.
CPC ..... *C12Q 1/6855* (2013.01); *C12Q 2525/191* (2013.01); *C12Q 2525/301* (2013.01); *C12Q 2531/125* (2013.01)

(58) Field of Classification Search
CPC ............ C12Q 1/6855; C12Q 2525/191; C12Q 2525/301; C12Q 2531/125
See application file for complete search history.

(56) References Cited

U.S. PATENT DOCUMENTS

| | | | |
|---|---|---|---|
| 6,235,502 | B1 | 5/2001 | Weissman et al. |
| 2003/0108902 | A1 | 6/2003 | Abarzua |
| 2005/0069939 | A1 | 3/2005 | Wang et al. |
| 2010/0120098 | A1 | 5/2010 | Grunenwald et al. |
| 2011/0118151 | A1 | 5/2011 | Eshoo et al. |
| 2011/0269193 | A1 | 11/2011 | Rhee et al. |
| 2013/0157870 | A1* | 6/2013 | Pushkarev ............ C12Q 1/6874 435/6.12 |
| 2016/0040143 | A1 | 2/2016 | Picher et al. |
| 2016/0053307 | A1 | 2/2016 | Heller et al. |
| 2019/0352706 | A1* | 11/2019 | Tsavachidou ........ C12Q 1/6869 |

FOREIGN PATENT DOCUMENTS

| | | |
|---|---|---|
| JP | 2016509853 A | 4/2016 |
| JP | 2017512071 A | 5/2017 |
| WO | 2007087262 A2 | 8/2007 |
| WO | 2010051773 A1 | 5/2010 |
| WO | 2011047307 A1 | 4/2011 |
| WO | 2013036685 A1 | 3/2013 |
| WO | 2014071070 A1 | 5/2014 |
| WO | 2014140309 A1 | 9/2014 |
| WO | 2015157747 A1 | 10/2015 |
| WO | 2015157747 A9 | 8/2016 |
| WO | 2016195963 A1 | 12/2016 |
| WO | 2017087823 A1 | 5/2017 |
| WO | 2017162754 A1 | 9/2017 |
| WO | 2019101596 A1 | 5/2019 |

OTHER PUBLICATIONS

EPO, International Search Report and Written Opinion dated Feb. 12, 2019, for PCT Application No. PCT/EP2018/081219, 18 pages.
Japanese Patent Office; Notice of Reasons for Rejection, Japanese Patent Application No. 2020-545440; dated Jul. 7, 2021, 12 pages.
Picher et al., "TruePrime is a novel method for whole-genome amplification from single cells base on TthPrimPol", Nature Communications, Nov. 29, 2016, 9 pages.
European Third Party Observations for Application No. 18811727.9, dated Feb. 25, 2022, 2 pages.
European, Communication for Application No. 18811727.9 dated Jun. 24, 2022, 10 pages.
Paez, J.G. et al. Genome coverage and sequence fidelity of ø29 polymerase-based multiple strand displacement whole genome amplification. Nucleic Acids Research, May 18, 2004, vol. 32, No. 9 pages e71:1-11.
Picher, A.J., TruePrime is a novel method for whole-genome amplification from single cells based on TthPrimPol, Nature Communications, Nov. 29, 2016, vol. 7, pp. 13296:1-13296:16.
Singapore, Written Opinion, Application No. 11202004534R, dated Jan. 18, 2022.
European Patent Office, Examination Report for 18811727.9 dated Apr. 14, 2023, 8 pages.
European Third Party Observations for Application No. 18811727.9, dated Oct. 6, 2023, 5 pages.
Singapore, Second Written Opinion, Application No. 11202004534R, dated Nov. 7, 2023, 5 Pages.

* cited by examiner

*Primary Examiner* — David C Thomas
(74) *Attorney, Agent, or Firm* — Storella & Witt, LLP

(57) ABSTRACT

Disclosed herein are devices and methods for amplifying double stranded DNA molecules. Methods for amplifying apoptotic cell-free DNA molecules can include performing end-repair and dA tailing of the cfDNA molecules, attachment of single-stranded hairpin adaptors to both ends of the end-repaired cfDNA molecules to produce adaptor-tagged, single-stranded, covalently closed DNA molecules, and amplification of the adaptor-tagged, single-stranded, covalently closed DNA molecules by a combination of rolling circle amplification and multiple displacement amplification using a PrimPol enzyme, a DNA polymerase with strand displacement activity and free nucleotides.

19 Claims, 21 Drawing Sheets
Specification includes a Sequence Listing.

Figure 7

Adaptors tested

Adaptor 1
$\quad\quad\quad\quad$ SEQ ID NO: 1
$_T{}^C{}^A$GGCCAACAAATGTTAT 3'
$\phantom{T}C_A$CCGGTTGTTTACAAT Adaptor 2
$\quad\quad\quad\quad$ SEQ ID NO: 2
$_T{}^C{}^T{}_T$GGCCAACAAATGTTAT 3'
$\phantom{T}C_C{}_T{}_T$CCGGTTGTTTACAAT Adaptor 3
$\quad\quad\quad\quad$ SEQ ID NO: 3
$_T{}^C{}^T{}^T{}_T{}_T$GGCCAACAAATGTTAT 3'
$\phantom{T}C_C{}_T{}_T{}_T$CCGGTTGTTTACAAT Adaptor 4
$\quad\quad\quad\quad$ SEQ ID NO: 4
$_T{}^C{}^T{}^T{}^T{}^T{}^T{}^T{}_T{}_T$GGCCAACAAATGTTAT 3'
$\phantom{T}C_C{}_T{}_T{}_T{}_T{}_T{}_T$CCGGTTGTTTACAAT

Figure 18

SEQ ID NO:10

```
MRPIEHALSYAAQGYGVLPLRFGGKEPLGKLVPHGLKNASRDPATLEAWWRSCPRCGVGILP
GPEVLVLDFDDPEAWEGLRQEHPALEAAPRQRTPKGGRHVFLRLPEGVRLSASVRAIPGVDL
RGMGRAYVVAAPTRLKDGRTYTWEAPLTPPEELPPVPQALLLKLLPPPPPRPSWGAVGTAS
PKRLQALLQAYAAQVARTPEGQRHLTLIRYAVAAGGLIPHGLDPREAEEVLVAAAMSAGLPE
WEARDAVRWGLGVGASRPLVLESSSKPPEPRTYRARVYARMRRWV
```

METHODS AND KITS FOR AMPLIFICATION OF DOUBLE STRANDED DNA

REFERENCE TO RELATED APPLICATIONS

This application is related to U.S. provisional application 62/589,074, filed Nov. 21, 2017.

STATEMENT AS TO FEDERALLY SPONSORED RESEARCH

None.

THE NAMES OF THE PARTIES TO A JOINT RESEARCH AGREEMENT

None.

SEQUENCE LISTING

Appended hereto.

BACKGROUND

The last 10 years have seen an enormous progress in both the understanding of cancer disease as well as the development of targeted therapies. An unprecedented number of new drugs has been approved for cancer treatment by the FDA and EMA over the course of the last 10 years[1]. Some of the most well-known drugs include Trastuzumab (Herceptin) for the treatment of breast cancer that targets the EGFR (HER2) receptor, Cetuximab (Erbitux) for the treatment of colorectal adenocarcinoma that targets the EGFR (HER1) receptor, Imatinib (Gleevec) for myeloproliferative disorders and CML targeting the Bcr-Abl fusion protein, Sorafenib (Nexavar) for liver and kidney cancer targeting several tyrosine protein kinases, Crizotinib (Xalkori) for the treatment of non-small cell lung carcinoma via inhibition of ALK-EML fusion proteins, or Vemurafenib (Zelboraf) for the treatment of melanoma via inhibition of the Braf V600E mutated kinase. The availability of a large set of targeted therapies has created the need for efficient molecular profiling of patients.

"Liquid biopsy" is a term coined to describe diagnostic procedures done on nucleic acids in the blood or in other bodily fluids (e.g. urine or cerebrospinal fluid (CSF)) of patients[2, 3, 4]. Cells dying by apoptosis or necrosis in a variety of diseases (cancer, myocardial infarction, transplant rejection) release DNA from their fragmented genomes into the bloodstream. Also, DNA from a fetus can be detected in the blood of the mother. A specific case are exosomes, 30-100 nm microvesicles, that next to DNA or RNA also contain proteins and lipids from the originating cell[5, 6, 7]. These nucleic acids in the blood can be detected and analyzed using PCR-based methods, next generation sequencing (NGS), or array technologies. Data that have been generated from analyzing liquid biopsies (e.g., nucleic acids obtained from bodily fluids rather than from tumor masses) have shown the enormous potential in this approach that could have a revolutionary impact on medical diagnosis, maybe similar only to the impact of the introduction of magnetic resonance imaging (MRI). Clinical applications that look particularly promising for the liquid biopsy approach are the diagnosis of chromosomal abnormalities in the fetus (in particular trisomy) by analyzing the blood from the mother (called also non-invasive prenatal screening (NIPT) based on cfDNA)[8, 9, 10, 11, 12, 13, 14, 15], the diagnosis and monitoring of graft rejection in transplantation patients (DNA from donor tissue attacked by immune cells of the host can be detected in the patient's blood)[16, 17, 18, 19, 20], and diagnosis and monitoring of cancer disease[2, 4, 21, 22, 23, 24, 25]. Areas with limited data so far are other diseases with tissue necrosis or apoptosis, such as myocardial infarction[26]. The use of "liquid biopsy" is most advanced in the detection of fetal chromosomal abnormalities (in particular trisomies) where genomic diagnosis is challenging the traditional combination of nuchal thickness measurement by ultrasound and the triple test (AFP, hCG, and estriol)[11]. However, the field with the promise of highest medical impact is clearly oncology, where data generated during the last few years have shown that key cancer mutations can principally be detected by liquid biopsy that mirror those present in traditional tumor biopsies[3, 27, 28].

Liquid biopsies may be superior to standard biopsies, as all parts of a tumor and all metastases are potentially sampled. Recent data indicate that in most cases analysis of circulating tumor DNA is faithfully reflecting mutations found in all known metastases of a cancer, or is even superior to such an approach (e.g. detecting mutations if standard biopsies fail, or showing more mutations than the standard tissue biopsies)[29], suggesting that sequencing circulating tumor DNA can give a much more complete molecular picture of the systemic cancer disease than standard biopsies. Also, access to a patient's blood is unproblematic. Serial liquid biopsies can be easily taken to monitor cancer therapy effects or to screen for reoccurrence of cancer as long as the volume of blood needed for the respective analysis is small (e.g. a few milliliters). Sensitivity of the method may be superior for detecting cancer at a very early stage, e.g. in cases of reoccurrence of cancer disease after curative surgery, or in a population-based screening program. If liquid biopsy can improve early detection of tumors in preventive screening programs will lead to a higher rate of cured cancer disease, especially for tumor types where means of early detection and preventive screenings are limited or non-existent.

Several studies of liquid biopsy approaches in cancer patients have revealed that the success rate of this approach is related to the tumor mass burden and tumor stage of a patient at the time of liquid biopsy, and the approach is not very successful in instances when tumor mass is low, because there are not so many tumor cells dying and releasing DNA into the blood[27, 30]. Moreover, the approach works well in some tumor types (e.g. colon carcinoma), but not in others (e.g. glioblastoma) presumably also due to sensitivity issues[27]. Limitations due to very small amounts of cfDNA are likely more relevant in cases where cfDNA is to be analyzed by whole exome or whole genome sequencing as opposed to very sensitive PCR-based approaches such as BEAMing[31]. Exome sequencing is advantageous to targeted PCR-based approaches, as practically the whole exome-based single-nucleotide mutation landscape can be analyzed as opposed to only few and pre-known mutations that can be assessed by targeted approaches. Therefore, exome sequencing has far more utility for early detection of cancer with high sensitivity, and of serial analyses of the changing clonal landscape of a tumor following treatment. Often, in research laboratories that have only access to standard library preparation and sequencing infrastructure, cell-free DNA amounts of 100 ngs are required for library construction[32]. With more specialized approaches, exome sequencing has been done from cfDNA amounts of a minimum of 2.3 ng[33]. Newman and colleagues have performed exome sequencing ("CAPP-seq") from down to 7 ng cfDNA[34]. De Mattos-Arruda used down to 22 ng of cfDNA input into library construction[35].

A second problem that can diminish the detection power of liquid biopsy approaches is the "contamination" of cell-free DNA with DNA coming from unrelated processes (e.g. nucleated blood cells lysis during plasma isolation). Cell-free DNA present in the blood plasma or other bodily fluids (CSF, urine, ascites) can be broadly divided into the smaller size fragments (140-160 and 2-3× multiples of this) that originate from apoptotic breakdown of genomic DNA inside a cell, and larger size fragments that originate mainly from necrotic cell death (necrosis), but also exosome shedding, and other less understood processes. DNA fragments of apoptotic origin can also be detected in healthy people and can increase after sports or a cold for example. Current techniques for cell-free DNA analysis are composed of two principal types of methodologies: A) Next-generation sequencing (NGS): next generation exome sequencing[33, 36], targeted (TAmseq[37]; CAPPseq[34]), FastSeqS[38], mFAST-SeqS[39], Safe-SeqS[40]), or whole genome sequencing[28]. Some commercial kits have also been used in this (e.g. Thermo Fisher Ion AmpliSeq Cancer Hotspot Panel v2). B) Digital PCR (BEAMing: beads, emulsions, amplification and magnetics[31, 41, 42, 43, 44]; digital PCR ligation assay[45]; emulsion based ddPCR with technology from RainDance or Bio-Rad).

WO 2014/140,309 refers to methods for replicating, amplifying, and sequencing of nucleic acids using the thermostable, bifunctional replicase "TthPrimPol" from *Thermus thermophilus* HB27. It has been found that purified TthPrimPol displayed a strong DNA primase activity on a single-stranded oligonucleotide in which a potential primase recognition sequence (GTCC) is flanked by thymine residues. Such a tract of pyrimidines has been shown to be the preferred template context for initiation of the priming reaction by several viral, prokaryotic and eukaryotic RNA primases. It has been found that priming occurred only in front of the "TC" sequence, and that there was no priming opposite the poly dT tracks. Further analysis of template sequence requirements revealed an effect of the nucleotide preceding the template initiation site on TthPrimPol's primase activity—C is preferred over A, G or T. Even if TthPrimPol prefers CTC as template initiation site, it is in general able to act as a primase on any sequence of the generic form XTC, where X stands for either of A, C, G, or T. The modest sequence requirement forms an excellent basis for random priming of nearly all natural templates.

Therefore, sensitivity and specificity limitations of current liquid biopsy approaches are an area in need of technical improvement.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 7 shows adaptors used to test the DNA primase activity of TthPrimPol.

FIG. 18 shows an amino acid sequence for TthPrimPol [SEQ ID NO: 10].

SUMMARY

Figure 1:
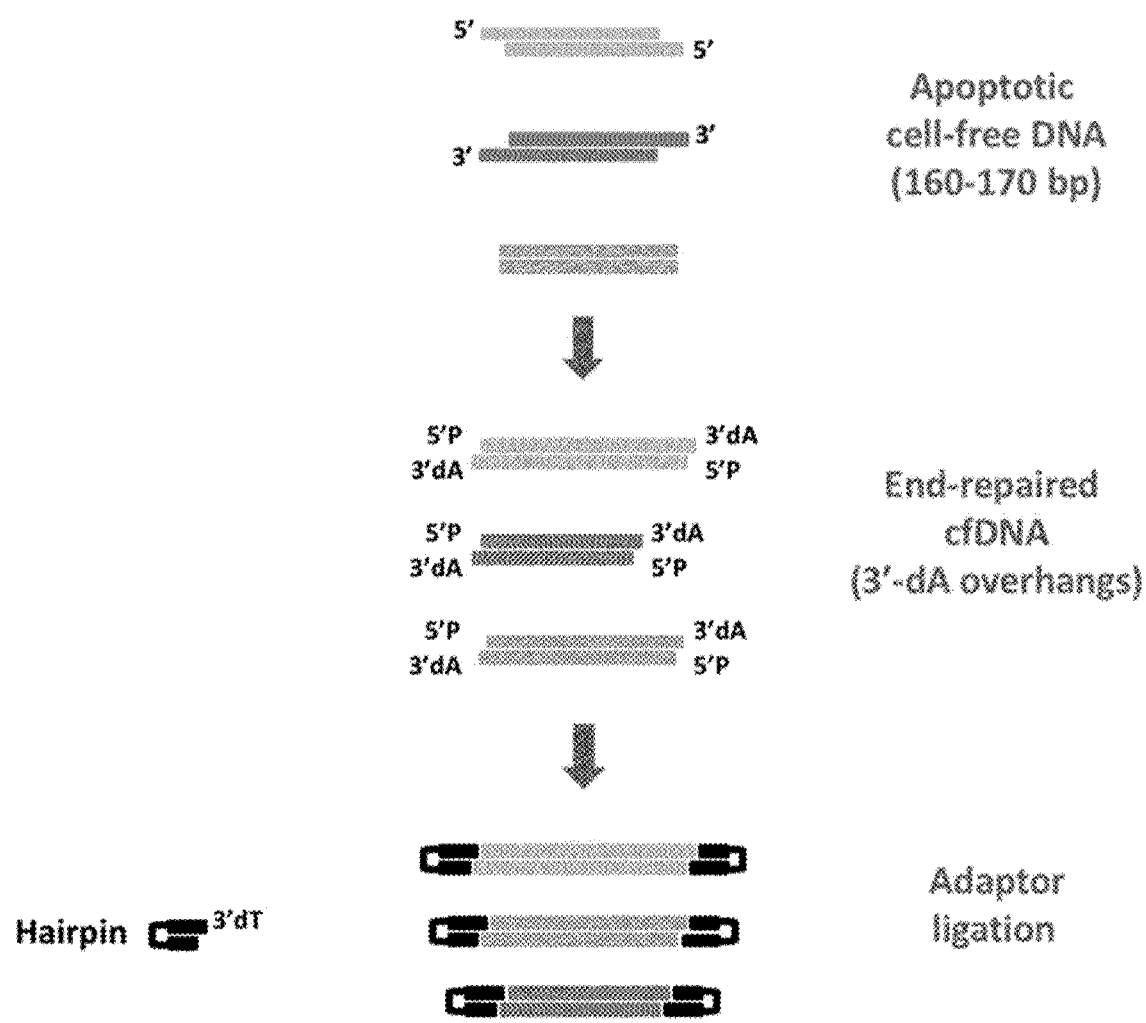
FIG. 1 shows cell-free DNA pretreatment to eliminate protruding ends, restore 5' phosphates and 3' hydroxyl groups, and add 3' dA overhangs.

Analysis of cell-free DNA in oncology and other fields offers huge opportunities to improve diagnosis and treatment in patients. A key problem is the difficulty to obtain results from biological fluids such as plasma, urine or CSF samples with very low cell-free DNA content. Methods disclosed herein provide a solution for this issue by amplifying short double-stranded polynucleotide fragments, including double-stranded DNA. This includes, without limitation those molecules found in cell-free DNA. Amplification is based on an amplification technology called "primase-initiated multiple displacement amplification" ("PI-MDA", also referred to as "TruePrime") combined with a novel set of sample pretreatments that allows its efficient amplification by subsequent steps such as rolling circle DNA amplification. As used herein, "primase-initiated multiple displacement amplification" or "TruePrime" refers to a form of multiple displacement amplification ("MDA") that uses a primase/polymerase to provide primers for primer extension by a DNA polymerase. Typically, the polymerase has a very strong displacement capacity and good fidelity of synthesis to avoid sequence changes during the process. One such polymerase is Phi29 DNA polymerase. While the current gold standard MDA needs short pieces of DNA ("oligonucleotides") to start off the amplification, primase-initiated multiple displacement amplification does not need any synthetic random primers.

The presently disclosed methods address, among other problems, this liquid biopsy sensitivity and specificity issue by an adapted amplification of apoptotic cell-free DNA based on the PI-MDA technology ("TruePrime"), which is a method of DNA amplification by iterative priming, copying and displacement steps.[46] TruePrime kits and protocols are available commercially from Expedeon AG and its affiliates. This disclosure provides a combination of existing TruePrime with the added steps of a sample pretreatment, comprising an end-repair, dA tailing, and the ligation of hairpin adaptors (see FIG. 1). Individually, these steps may be carried out by methods known in the art, including by use of the New England Biolabs NEBNext Ultra II DNA Library Prep Kit and similar products and methods, and/or for example: (a) for end repair T4 polynucleotide kinase (PNK)+T4 DNA polymerase Klenow fragment and T4 DNA polymerase large fragment are commonly used (b) for dA tailing Taq polymerase is commonly used. This novel combination of methods provides an efficient process for what would otherwise be unworkable or inefficient: the amplification of small fragments of DNA by traditional TruePrime or other methods. The method steps may optionally be followed by the rolling circle DNA amplification method (see FIG. 2). Thus, we provide a novel method to amplify short DNA molecules, e.g. but not limited to, apoptotic cell-free DNA without ligation, allowing an increase in the DNA available for any analytical technology, with superior sensitivity and specificity. While the methods disclosed herein provide particular advantage for short DNA fragments they also work well with DNA samples of any length.

DETAILED DESCRIPTION

I. Introduction

PrimPol is an enzyme obtained from the thermophilic bacteria *Thermus thermophilus*. PrimPol combines two distinct and complementary activities in a single thermo-stable protein: primase and polymerase. Conventional polymerases require small stretches of nucleotides (primers) annealed to a template molecule to synthesize the complementary sequence. PrimPol, on the contrary, creates its own primer sequence, thereby offering fully novel applications.

Moreover, PrimPol is able to copy both DNA and RNA. RNA reflects what genetic information is actually expressed in a cell, whereas DNA refers to the general genetic information present in every cell in the body and often only reflects a predisposition of a person to develop a disease. The development of PrimPol will help to simplify technical aspects of DNA and RNA amplification procedures.

PrimPol also shows a great tolerance to damaged DNA. DNA is subject to chemical modifications within the cells. Also during the processes necessary to purify the genetic material, and storage of forensic and clinical samples (e.g. formalin-fixed paraffin-embedded tissues) trigger such modifications. Chemical modifications have been shown to play an increasingly important role in several biological processes, such as aging, neurodegenerative diseases, and cancer. Therefore, there is great interest to develop methods for interrogating damaged DNA in the context of sequencing. Thus, an enzyme able to handle modified templates is of particular interest, since current amplification applications as well as second and third generation sequencing technologies are not optimized to use damaged samples.

PrimPol is also suited to be used in different second and third generation sequencing technologies due to its ability to introduce a variety of substrate nucleotides (e.g. fluorescent nucleotides) into DNA and RNA template molecules.

Finally, PrimPol has a role in multiple displacement amplification (MDA) reactions, generating primers for its subsequent use by Phi29 DNA polymerase, thus making unnecessary the use of random synthetic primers and possibly resulting in a more uniform amplification of DNA.

II. Methods of Amplifying Linear Double Stranded Polynucleotides

Provided herein are, among other things, methods of amplifying linear, double stranded polynucleotides (e.g., DNA molecules) and, in particular, apoptotic (mononucleosomal) cell-free DNA. Methods of amplifying linear, double stranded DNA include attaching single-stranded hairpin adaptors to both ends of the DNA molecules to produce single stranded, covalently closed DNA molecules and amplifying the covalently closed DNA molecules by rolling circle amplification and multiple displacement amplification, e.g., primase-initiated multiple displacement amplification.

A. Linear Double Stranded DNA

Linear double stranded DNA for use in the amplification methods described herein can be provided from any source. This includes, for example, DNA from eukaryotes, eubacteria, archaebacteria and viruses. Eukaryotic sources of DNA can include plants, animals, vertebrates, mammals, and humans. Microbial sources of DNA can include microbes sourced from a microbiome of an individual or from the environment.

The linear double stranded DNA used in the amplification methods disclosed herein can be of any length. In certain embodiments, the linear double stranded DNA has a length of no more than 5000 nucleotides, no more than 1000 nucleotides, no more than 500 nucleotides or no more than 200 nucleotides. In other embodiments the population of linear double stranded DNA molecules to be amplified can have an average length of no more than 5000 nucleotides, no more than 1000 nucleotides, no more than 500 nucleotides, no more than 200 nucleotides, no more than 100 nucleotides, no more than 50 nucleotides, no more than 20 nucleotides, e.g., about 168 nucleotides. DNA molecules to be amplified can include molecules having a length between about 100 and about 220 nucleotides. The linear double stranded DNA can comprise fragmented chromosomal DNA. Such DNA fragments may have a length greater than 5000 nucleotides.

Nucleic acids are typically isolated from other components by isolation methods well known in the art including, without limitation, capture on particles having DNA or RNA binding activity, such as silica particles; polyethylene glycol precipitation and SPRI (Solid Phase Reversible Immobilization) beads.

1. Cell-Free Polynucleotides

The linear double stranded DNA used in the methods disclosed herein can comprise cell-free DNA ("cfDNA"). Cell-free DNA refers to DNA that is not encapsulated inside a cell. Cell-free DNA can be apoptotic cell-free DNA. (FIG. 1, "Apoptotic cell-free DNA".) Apoptotic cfDNA refers to DNA released from dead or dying cells, e.g., through the apoptosis cell death mechanism, in which the DNA is cut between nucleosomes, producing DNA fragments of 160-170 bp, or multiples thereof, when the cut in the DNA is not produced between every nucleosome. This includes DNA released from normal cells, e.g. having a germline genome. It also includes DNA released from cancer cells (e.g. malignant cells), also referred to as circulating tumor DNA or "ctDNA". This DNA typically carries somatic mutations associated with cancer e.g., in oncogenes or tumor suppressor genes. Apoptotic cfDNA also includes fetal DNA in the maternal circulation. Cell free DNA can be sourced from any of a number of different bodily fluids including, without limitation, blood, plasma, serum, CSF, urine, saliva, tear drops, milk, semen and synovial fluid. Apoptotic cfDNA typically has a size distribution with two peaks; a first mononucleosomal peak between about 110 to about 230 nucleotides, with a mode of about 168 nucleotides, and a second, minor dinucleosomal peak between about 240 to 440 nucleotides.

Cell-free DNA molecules can be prepared from bodily fluids, such as blood, by conventional methods. Commercial kits for this purpose are available from, e.g., Thermo Fisher Scientific (Waltham, MA, USA), Active Motif (Carlsbad, CA, USA) and Qiagen (North Rhine-Westphalia, Germany). In general, cells are removed from a sample, for example by centrifugation. Silica particles, e.g. magnetic silica beads, are added to the sample from which cells have been removed. The silica particles bind the DNA. The particles are isolated from the supernatant, for example by centrifugation and/or application of magnetic force. Supernatant is removed and the particles are washed. Cell-free DNA is isolated from the particles by dilution with ethanol.

2. Other Polynucleotides

In other embodiments, the double stranded DNA molecules comprise fragmented genomic DNA, for example, isolated from cells or double stranded cDNA molecules produced from reverse transcription of RNA molecules, such as mRNA, rRNA or tRNA molecules.

3. End-Repair

End-repair refers to a process of providing double stranded DNA molecules having 3' and/or 5' single strand overhangs with either sticky ends or blunt ends. End repair renders double stranded DNA molecules more suitable for attachment to polynucleotide adaptors. Attachment can be by either sticky-end ligation or blunt-end ligation. "Sticky-end ligation" refers to the ligation of two double-stranded polynucleotides, each of which has a 3' overhang complementary to the other 3' overhang. A sticky end can be, for example, a single nucleotide overhang, such as 3' dA and 3' dT, or a longer sticky-end, such as an overhang produced by restriction enzyme digestion. "Blunt-end ligation" refers to the ligation of a double stranded polynucleotide to the blunt-end of another, double stranded polynucleotide.

In either case, modification of the polynucleotide typically initially involves blunt ending the molecules. Typically, this involves using a polymerase to fill in a 5' overhang and a molecule having exonuclease activity to chew back a 3' overhang. Blunt-ending can be performed using a mixture of T4 polymerase and the DNA polymerase I klenow fragment. The klenow fragment possesses 5'-3' polymerase activity to fill in 5' overhangs and 3'-5' exonuclease activity to remove 3' overhangs. T4 DNA polymerase possesses a less efficient 5'→3' polymerase activity and a more efficient 3'-5' exonuclease activity. Mung bean nuclease also can be used to eliminate 5' and 3' overhangs. T4 polynucleotide kinase ("T4 PNK") is used to phosphorylate the 5' strand of a molecule and dephosphorylate the 3' strand. Kits for performing blunt-ending of DNA molecules are available from a variety of commercial sources including Thermo Fisher Scientific (Waltham, MA, USA) and New England Biolabs (Ipswich, MA, USA).

In certain embodiments, a blunt-ended polynucleotide can be dA-tailed by a process of adding a terminal 3' deoxy adenosine nucleotide to a DNA molecule. This action can be performed using Taq polymerase. (FIG. 1, "End-repaired cfDNA (3'-dA overhangs)".)

Blunt-ended molecules or dA-tailed molecules can be used in the methods described herein by the attachment of single-stranded adaptors.

B. Attachment of Single-Stranded Adaptors

Polynucleotides that have been end-repaired and, optionally, dA-tailed, can be ligated to adaptors. Adaptors are polynucleotide molecules adapted for attachment to target molecules. Typically, adaptors include nucleotide sequences for priming DNA strand extension. In certain methods of this disclosure the adaptor is a hairpin adaptor. As used herein, the term "hairpin adaptor" refers to a single stranded nucleic acid molecule (e.g., DNA) that includes a second region flanked by a first and third region. The first and third regions have sufficient complementarity to hybridize with each other (e.g., 95%, 99%, or 100% complementary). The second region is not complementary to either the first or the third region. The adaptor can have a length of between 25 and 100 nucleotides long. The second region can be, for example, 4, 5, 6, 7, 8, 9, 10, 11, 12, 13, 14, 15, or fewer than 25 nucleotides long. As a consequence, a hairpin adaptor molecule can fold back on itself forming a stem-and-loop structure comprising a double stranded end and a single-stranded, internal segment that is not hybridized. Hairpin adaptors can include a 3' dA overhang, or be blunt-ended, depending on the application. See, e.g., FIG. 7 and FIG. 8.

Adaptors also typically include internal nucleotide sequences compatible with a DNA primase and/or primer extension. For example, the hairpin adaptor can include a primase/polymerase recognition sequence, e.g., XTC, where X represents nucleotides a, T, G or C, for example, CTC, GTC or GTCC. The primase/polymerase recognition sequence can be located in the loop (non-complementary) portion of the adapter. Which is recognized by TthPrimPol. In other embodiments the hairpin adaptor comprises an amplification primer binding site.

End repaired, dA-tailed double-stranded polynucleotides can be attached on one or both ends to hairpin adaptors. The end of the adaptor is preferably compatible with the end of the double stranded polynucleotide. So, for example, a dA-tailed double-strand polynucleotide is attached to a dT tailed hairpin adaptor, or a blunt-ended double-stranded polynucleotide is attached to a blunt-ended hairpin adaptor.

Attachment is typically performed with a DNA ligase, such as T4 DNA ligase. In certain embodiments hairpin adaptors have a sequence as depicted in FIG. 7, i.e., [SEQ ID NO:1], [SEQ ID NO:2], [SEQ ID NO:3], or [SEQ ID NO:4].

The product of ligation between hairpin adaptors and double-stranded polynucleotides is a single-stranded, covalently closed polynucleotide. See, e.g., FIG. 1 ("Adaptor ligation"). Such a polynucleotide can also be described as a single stranded, circular polynucleotide. As used herein, the term "covalently closed DNA molecule" refers to a DNA molecule having no free 5' or 3' end. Such molecules are also referred to as "circular DNA". Because they have complementary internal sequences, such molecules can assume a "dumbbell" shape. A polynucleotide insert flanked on one or both ends by hairpin adaptors is referred to as a "adaptor-tagged polynucleotide".

A collection of adaptor-tagged polynucleotides is referred to as a "nucleic acid library". Typically, in the case of cfDNA, a nucleic acid library comprising a population of end-repaired DNA molecules include polynucleotide inserts having different nucleotide sequences.

Single-stranded, covalently closed polynucleotides can be amplified by methods disclosed herein.

C. Amplification

In certain embodiments, amplification of single-stranded, covalently closed polynucleotides involves using a DNA-directed primase/polymerase, such as TthPrimPol; a DNA polymerase having strand displacement activity, such as Phi29; and modified or unmodified deoxyribonucleotides. In combination, these reagents effect rolling circle amplification primed by the primase/polymerase and extended by the DNA polymerase. Furthermore, the combination of primase/polymerase and DNA polymerase can effect multiple strand displacement amplification through priming of amplified molecules with the primase/polymerase and/or random oligonucleotide primers and primer extension by the DNA polymerase. Multiple strand displacement amplification produces a branched structure as DNA synthesis is primed and extended from many positions in the amplified molecules.

Furthermore, amplification can be accomplished without the use of oligonucleotide primer molecules by using hairpin adaptors comprising one or more primase recognition sites together with a primase having DNA priming activity on single stranded DNA, such as TthPrimPol, and a DNA polymerase having strand displacement activity, such as Phi29 and deoxyribonucleotide triphosphates. Using these reagents, a highly branched structure is produced during multiple strand displacement amplification.

1. Primase/Polymerase

As used herein, the term "priming" refers to the generation of an oligonucleotide primer on a polynucleotide template.

For amplification of DNA, the primase/polymerase can be a DNA-directed primase/polymerase, such as a PrimPol enzyme. Unlike most primases, PrimPol is uniquely capable of starting DNA chains with dNTPs. Useful PrimPol enzymes include, among others, *Thermus thermophilus* primase/polymerase ("TthPrimPol") and human primase/polymerase ("hsPrimPol").

*Thermus thermophilus* HB27 primase/polymerase is described, for example, in WO 2014/140309, published Sep. 18, 2014 ("Methods for amplification and sequencing using thermostable TthPrimPol"). It has an amino acid sequence shown in FIG. 18 [SEQ ID NO: 10]. It bears Gene ID: NC_005835 in the NCBI Entrez database, protein WP_011173100.1 TthPrimPol can be obtained commercially in kits from Expedeon (Cambridge, UK).

Human PrimPol is also known as MYP22; CCDC111 and Primpol1. It bears Gene ID: 201973 in the NCBI Entrez database.

The PrimPol can be a relative of any PrimPol described herein including the following: An allelic variant (a naturally occurring variation of a gene), an artificial variant (a gene or protein comprising one or more genetic modifications to a naturally occurring gene or protein while retaining natural function), a homolog (a naturally occurring gene from another genus or species than the one defined, or a distinct gene in the same strain or species that encodes for a protein having nearly identical folding and function); an ortholog (a homolog that occurs in another genus or species from the one discussed) or a paralog (a homolog that occurs in the same strain or species as the one discussed, e.g., as a result of gene duplication). A PrimPol enzyme can have at least 80%, 85%, 90%, 95%, 98% or 99% amino acid sequence homology with the protein of SEQ ID NO: 10.

2. DNA Polymerase with Strand Displacement Activity

Amplification methods can employ a DNA polymerase with strand displacement activity, e.g., a polymerase with strong binding to single-stranded DNA e.g., in preference to double-stranded DNA. Strand displacement activity can be useful in displacing hybridized strands of a DNA molecule while extending a primer position, for example, in the loop area of a hairpin structure.

DNA polymerases with strand displacement activity useful in methods disclosed herein include, for example, Phi29. Phi29 DNA polymerase can be obtained commercially from, for example, New England Biolabs (Ipswich, MA, USA), ThermoFisher Scientific (Waltham, MA, USA and Expedeon (Cambridge, UK). Phi29 polymerase can generate DNA fragments up to 100 kb. The enzyme has a 3'-5' exonuclease proofreading activity and provides up to 1000-fold higher fidelity compared to Taq DNA polymerase-based methods. Phi29 polymerase can function on DNA comprising secondary structures such as hairpin loops.

In another embodiment the DNA polymerase can be Bacillus steatothermophilus (Bst) polymerase.

3. Deoxyribonucleotide Triphosphates

Primer creation and primer extension can be accomplished by providing primase/polymerase enzymes and DNA polymerases with deoxyribonucleotide substrates e.g., deoxyribonucleotide triphosphates. Typically, these include the four standard bases, A, T, G and C. However, in certain embodiments non-natural nucleotides, such as inosine can be included. In certain embodiments nucleotides may bear a label for detection or capture of polynucleotides into which they are incorporated.

4. Rolling Circle Amplification

Rolling circle amplification is a method of amplifying a covalently closed DNA molecule such as a single stranded, covalently closed DNA molecule. The template DNA molecule is primed with a primer, for example a primer provided by a primase/polymerase. A DNA polymerase performs primer extension on the primer around the closed DNA molecule. The polymerase displaces the hybridized copy and continues polynucleotide extension around the template to produce a concatenated amplification product.

5. Multiple Displacement Amplification

Multiple displacement amplification is an isothermal, non-PCR-based DNA amplification method in which primer extension from a template molecule produces molecules which themselves are primed and copied by primer extension to produce a branch-like structure. Branches are displaced from each other as primers are extended from one DNA molecule template into the branch area. In certain embodiments MDA employs random hexamers as primers to prime amplification at multiple sites on an original template and amplified copies thereof. Multiple strand amplification is further described in, for example, WO2011/047307A1, published Apr. 21, 2011 ("Multiple Displacement Amplification"). Polymerization that extends primers at multiple priming sites.

In certain embodiments of the disclosed methods, priming is accomplished with a primase/polymerase, such as TthPrimPol. In this case priming includes the provision of deoxyribonucleotide triphosphates as a reagent. In certain embodiments, the deoxyribonucleotides are unmodified. In other embodiments, deoxyribonucleotides can be modified by attachments to a label, for example, a fluorescent molecule. As used herein, the term "label" refers to a chemical moiety attached to a molecule, such as a nucleic acid molecule. Detectable labels include, for example, fluorescent labels, luminescent labels, enzymatic labels, colorimetric labels such as colloidal gold or colored glass or plastic beads and radioactive labels.

Figure 2:
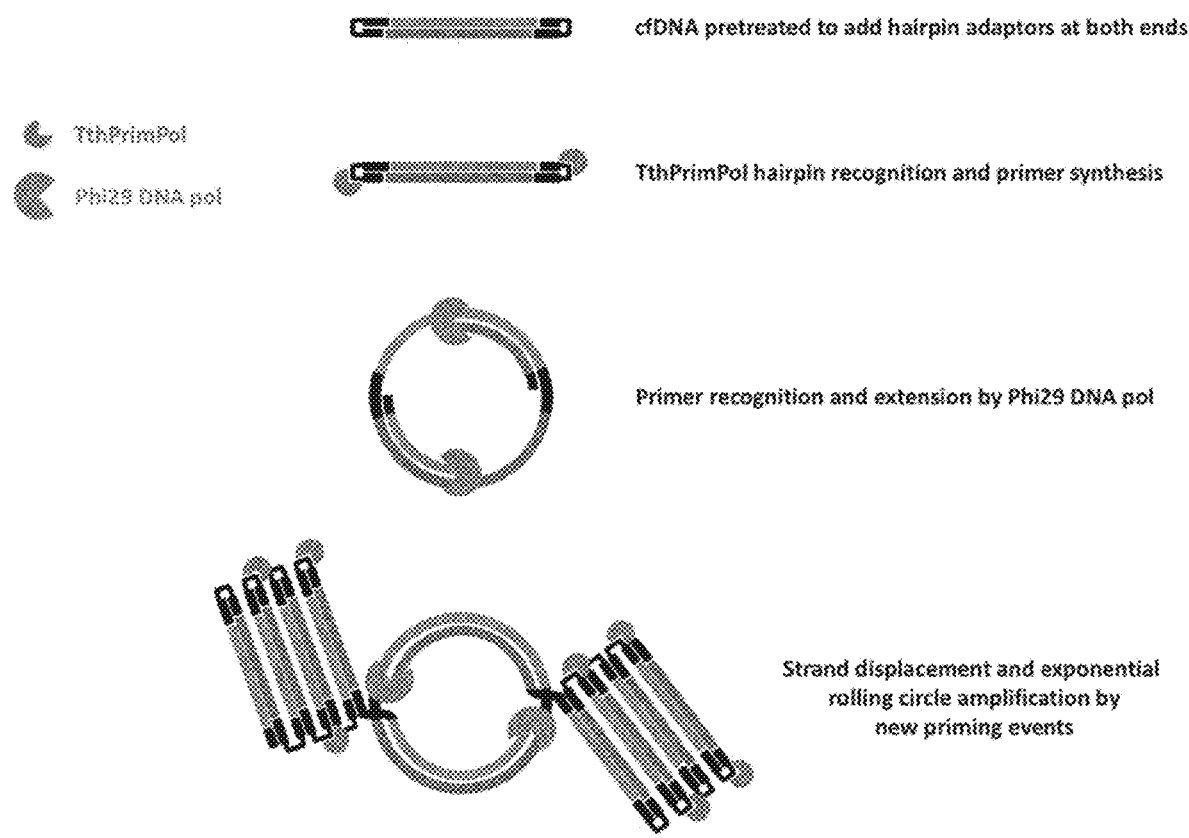
FIG. 2 shows a mechanism of an amplification kit for apoptotic cell-free DNA.

Referring to FIG. 2, in methods disclosed herein, a single stranded, covalently closed nucleic acid molecule template ("cfDNA pretreated to add hairpin adaptors at both ends") is provided. A primase/polymerase, such as TthPrimPol, is provided and recognizes recognition sites in the hairpin adapter and primes polymerization by the synthesis of primers. ("TthPrimPol hairpin recognition and primer synthesis".) A DNA polymerase with preference for binding single-stranded nucleic acid molecules and strand displacement activity amplifies the template through a combination of rolling circle amplification and multiple displacement amplification. Rolling circle amplification provides a concatenated molecule that folds back on itself forming double-stranded segments based on the complementary sequences. These folds also include the adapter sequences comprising primase/polymerase recognition sites. The primase/polymerase synthesizes primers on the concatenated molecule which are, in turn, extended by the DNA polymerase. The result is exponential amplification of the original template molecule, typically in branched fashion. ("Stranded displacement and exponential rolling circle amplification by new priming events".)

6. Other Amplification Methods

Contemplated herein are other methods of amplifying single-stranded, covalently closed DNA molecules.

In one method, rather than priming polymerization with a primase/polymerase, amplification is primed with random sequence primers. For example, random sequence primers can be hexamers comprising a degenerate set of sequences. Amplification can continue by multiple displacement amplification.

In another method, amplification of single-stranded, covalently closed DNA molecules is performed by Degenerate Oligonucleotide Primed (DOP)-PCR. (DOP)-PCR uses a single primer for PCR (instead of a forward and reverse primer). This primer is usually an oligomer having about 22 bases with a six-nucleotide degenerate region in the center, e.g. 5'CGACTCGAGNNNNNNATGTGG 3' [SEQ ID NO: 9]. This degenerate region is a random sequence composed of any of the four DNA nucleotides. The first five steps of the DOP-PCR procedure are a non-specific amplification step. The degenerate primer along with low annealing temperatures will cause random annealing at locations across the entire genome. During PCR, extension will occur from these primers and create long fragments.

In another method, amplification of single-stranded, covalently closed DNA molecules is performed by Primer Extension Preamplification (PEP). Primer Extension Preamplification (PEP) uses random/degenerate primers and a low PCR annealing temperature. The primers can be, for example, about 15 nucleotides long.

In another method, amplification of single-stranded, covalently closed DNA molecules is performed by linker-adaptor PCR (LA-PCR). In LA-PCR, double-stranded DNA is digested with MseI, leaving a TA overhang for adapter annealing and subsequent ligation. A single primer, complementary to the adapter, is used to amplify the whole sample by PCR.

In another method, amplification of single-stranded, covalently closed DNA molecules is performed by using any combination of a thermostable DNA polymerase (e.g., Taq polymerase) and a highly processive strand-displacement DNA polymerase (e.g., Phi29 polymerase or Bacillus stearothermophilus (Bst) polymerase). One such method is Multiple Annealing and Looping Based Amplification Cycles (MALBAC). MALBAC is a non-exponential whole genome amplification method. Primers used in MALBAC allow amplicons to have complementary ends which form loops, inhibiting exponential copying.

D. DNA Sequencing

As used herein, the term "high throughput sequencing" refers to the simultaneous or near simultaneous sequencing of thousands of nucleic acid molecules. High throughput sequencing is sometimes referred to as "next generation sequencing" or "massively parallel sequencing". Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore).

Methods described herein can be used for, without limitation, whole genome sequencing, exome sequencing and amplicon sequencing. To the extent apoptotic cfDNA comprises sequences from the entire genome, the amplification product of methods described herein represent whole genome amplification. However, amplified molecules themselves, can be subject to amplification of specific amplicons. Sequence capture using baits directed to gene sequences in the genome can be used to isolate amplified molecules representing the exome. By reverse transcribing mRNA into double stranded cDNA an amplified transcriptome can be produced for sequencing.

DNA amplified by the methods disclosed herein has properties of double-stranded DNA. This is due, at least in part, to the complementarity within strands which fold back on themselves. Accordingly, amplified DNA can be prepared for sequencing as one might native double-stranded DNA. Library preparation methods depend on both the sequencing platform and the sequencing approach. For example, the sequencing platform may be adapted for short reads, such as Illumina or Ion Torrent, or for long reads, such as PacBio or Oxford Nanopore. Sequencing approaches include targeted, whole exome or whole genome sequencing. For example, to perform whole genome sequencing using Illumina, one can shear the DNA (enzymatically or mechanically) to a length appropriate to the sequencing specifications (e.g., single-end or paired-end reads and chosen lengths (150 nucleotides, 250 nucleotides, etc.). After shearing, the libraries are prepared using kits that include the adaptors suitable for the sequencing to occur. In contrast, when using long-read whole genome sequencing, e.g., PacBio and Oxford Nanopore, a first step with T7 endonuclease is recommended to eliminate the multi-branched DNA structure derived from the multiple displacement amplification mechanism produced by all MDA methods. Otherwise, different library prep methods are followed depending on the sequencing platform. In targeted approaches, PCR is used to amplify certain regions of interest, that will be the only ones sequenced afterwards.

III. Kits

Also provided herein are kits for use in performing the methods disclosed herein. As used herein, the term "kit" refers to a collection of items intended for use together.

Certain kits disclosed herein include 2, 3, 4, 5, 6, 7, elements selected from: (1) a PrimPol enzyme (e.g., TthPrimPol); (2) a DNA polymerase (e.g., Phi29); (3) a single strand hairpin adaptor; (4) one or more enzymes for dsDNA end repair (e.g., T4 DNA polymerase, klenow fragment and/or Taq polymerase); (5) one or more enzymes for DNA ligation; (6) dNTPs; (7) an enhancer, e.g. to increase DNA ligation efficiency, e.g., polyethylene glycol; (8) reaction buffer and (9) a buffer for use with any of the aforementioned elements. The kits can comprise containers to hold these reagents for. Kits can include containers to hold reagents. Containers, themselves, can be placed into a shipping container. The container can be transmitted by hand delivery or by a common carrier, such as a national postal system or a delivery service such as FedEx. Kits also can contain a container for shipping collected blood to a central facility, such as a box or a bag. Kits can also typically include instructions for use as well as and software for data analysis and interpretation.

EXAMPLES

Example 1

Figure 3:
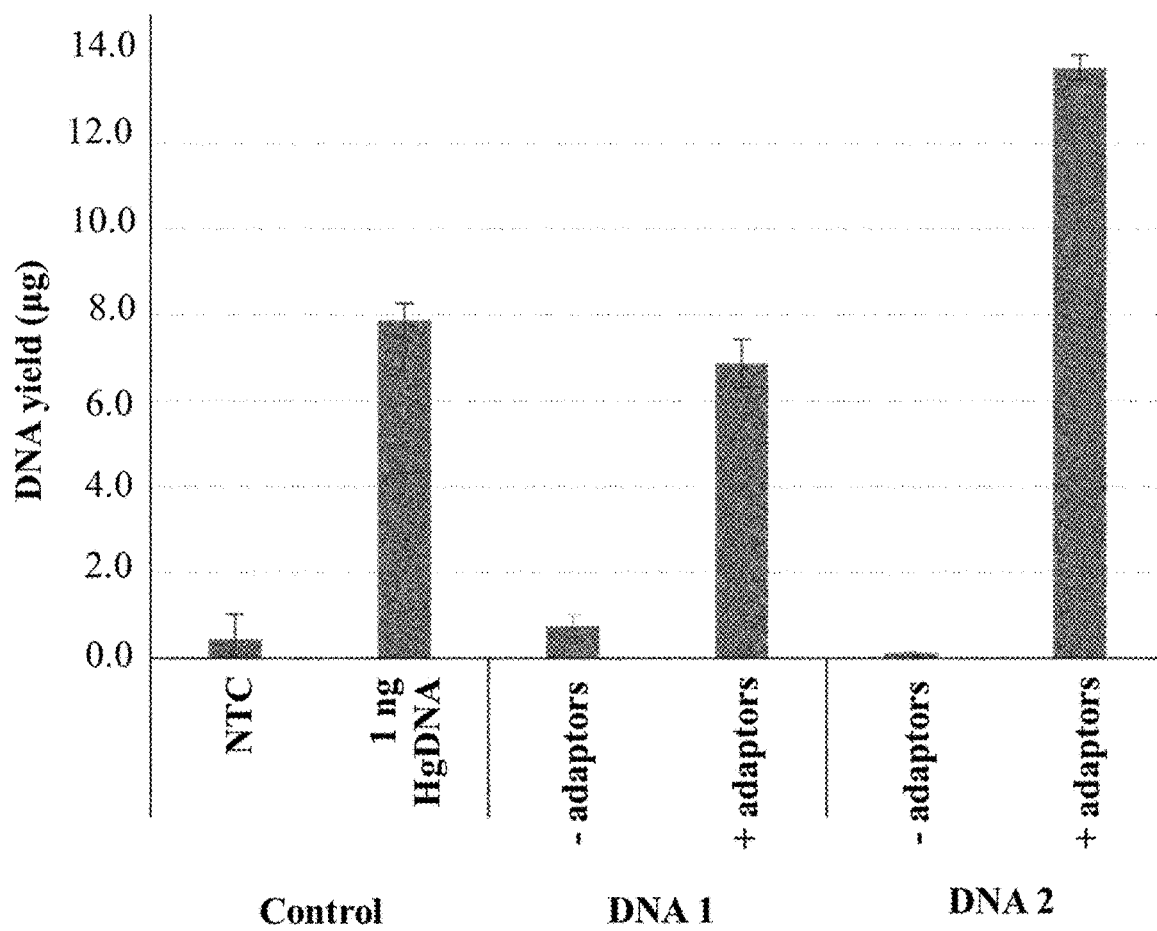
FIG. 3 shows evidence that TruePrime technology requires the addition of hairpin adaptors to efficiently amplify short DNA molecules (200 bp) by primase-initiated multiple displacement amplification. "NTC" refers to "non-template control" (no DNA is added as input for the reaction). "HgDNA" stands for human genomic DNA.

Hairpin Addition at Both DNA Ends According to the Disclosure Allows the Efficient Amplification of Short DNA Molecules by TruePrime Multiple Displacement Amplification Shown in FIG. 3 is the amplification of short DNA molecules (200 bp) obtained by PCR amplification. The end-repair and dA-tailing reaction, and the addition of the hairpin adaptors enables the efficient amplification of the short DNA input by TruePrime.

Figure 4:
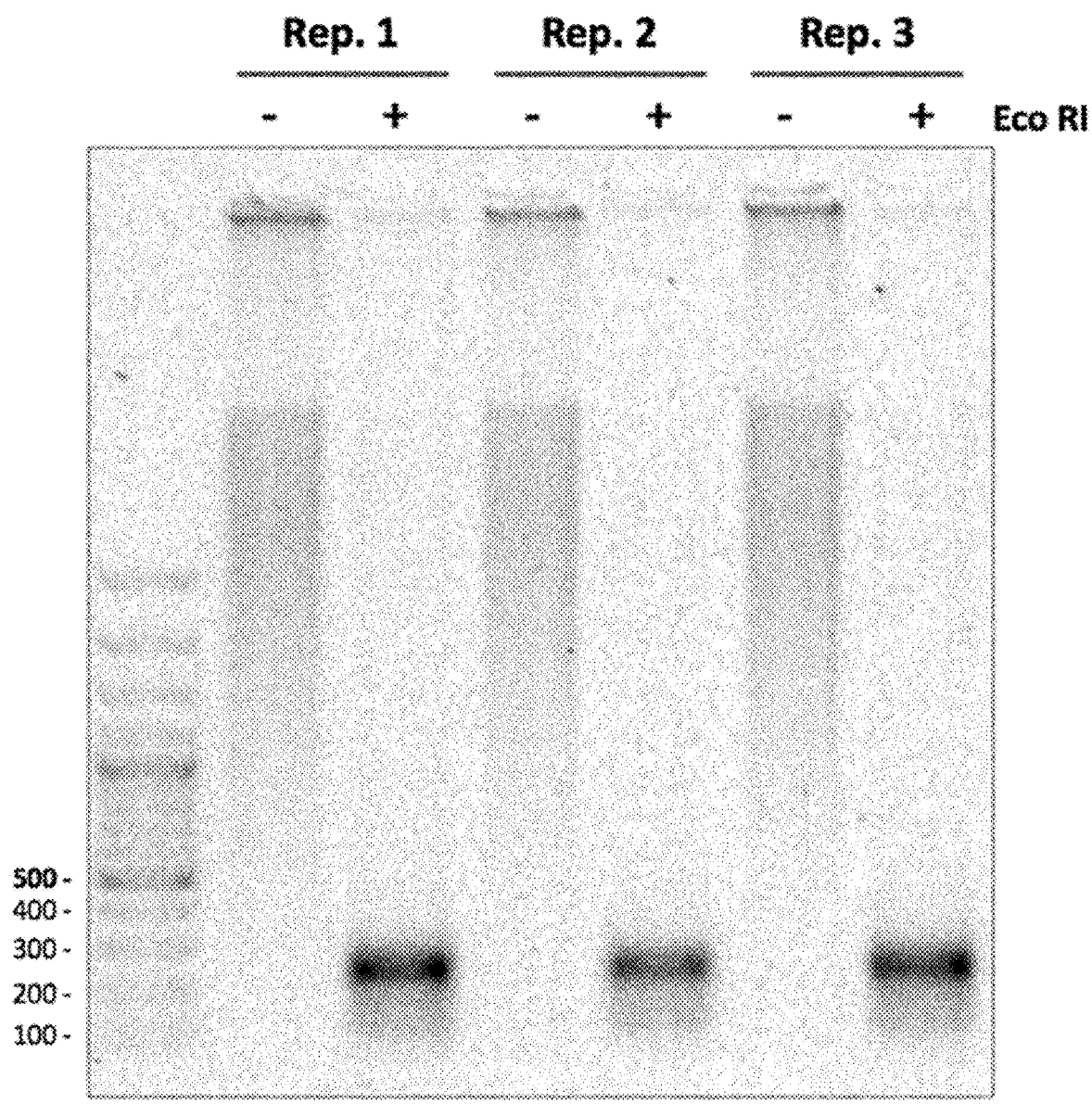
FIG. 4 shows amplified DNAs (3 independent replicates) from FIG. 3 (DNA 1) that were cut with EcoRI restriction enzyme obtaining the expected unit size (200 bp from the original DNA fragment+36 bp from the hairpin adaptor).

The presence in DNA 1 of a single restriction recognition site for EcoRI enzyme allowed us to obtain single units of the amplified material (see FIG. 4), demonstrating the amplification mechanism illustrated in FIG. 2.

Example 2

Figure 5A:
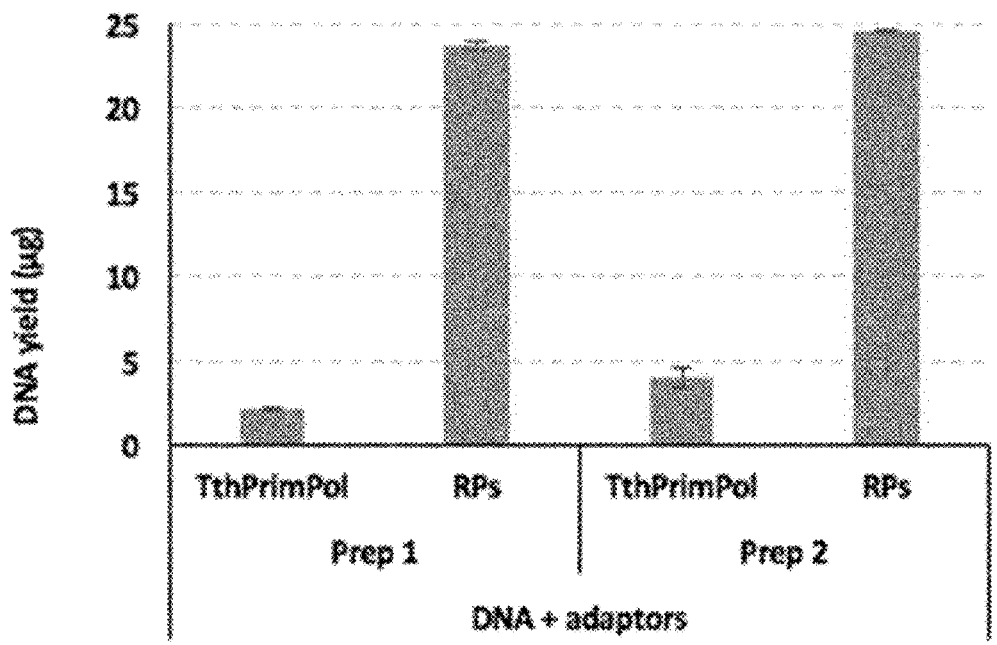
FIGS. 5A and 5B show amplification yields (5A, upper part) depending on the method used to initiate the amplification (TthPrimPol or random primers) and the result of the digestion with a restriction enzyme of each amplified DNA (5B, lower part).
Figure 5B:
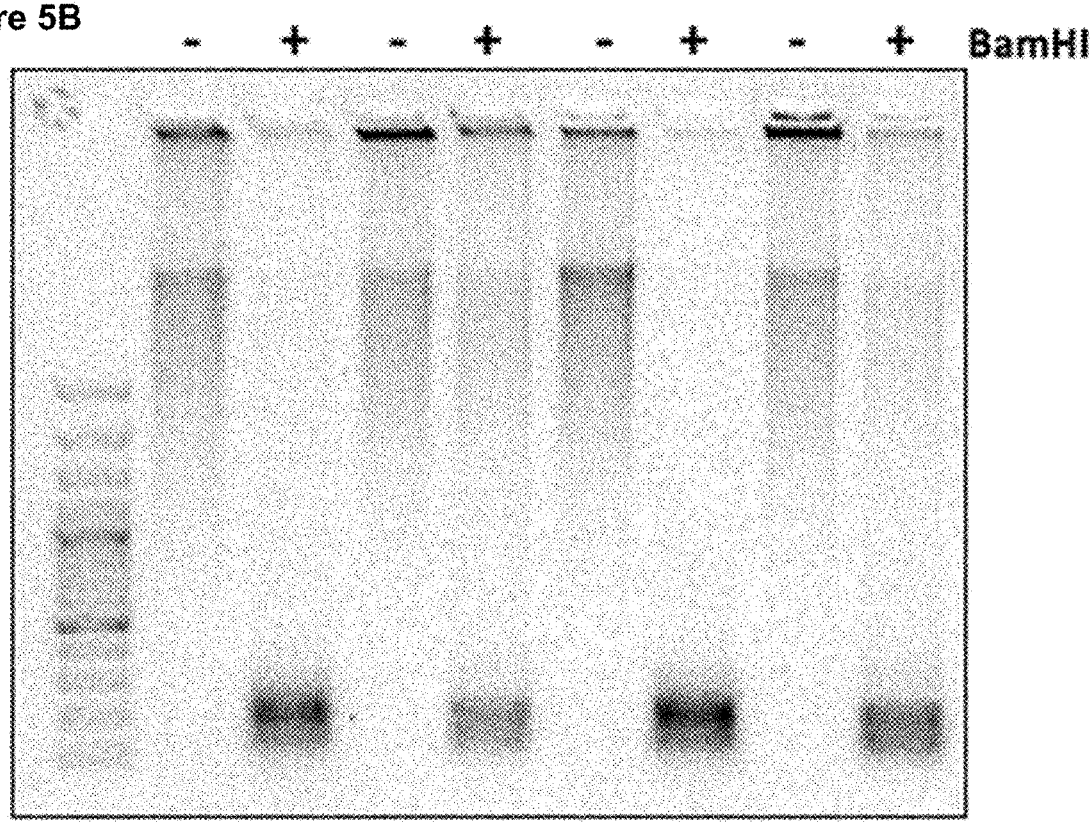

TruePrime Rolling Circle Amplification Shows More Specific Amplification of the Target Molecule than MDA Methods Based on Random Synthetic Primers Shown in FIG. 5 is the amplification of short DNA molecules (200 bp) obtained by PCR amplification and subjected to the procedure of the disclosure: end-repair, dA-tailing, hairpin-adaptor ligation and rolling circle amplification. The rolling circle amplification can be carried out either with TthPrimPol (TruePrime) or random synthetic primers (RPs) to trigger the amplification, using two independently-prepared DNA samples as substrate (Prep 1 and Prep 2). The amplification yield is much higher when using random primers (see FIG. 5 upper part). However, the analysis of the same amount of amplified DNA (500 ng) by restriction enzyme digestion reveals that TruePrime (based on TthPrimPol) produces more target molecules (236 bp) than random primers, probably due to the amplification of primer dimers, which is a well-known drawback of MDA methods based on random synthetic primers.

Example 3

Figure 6:
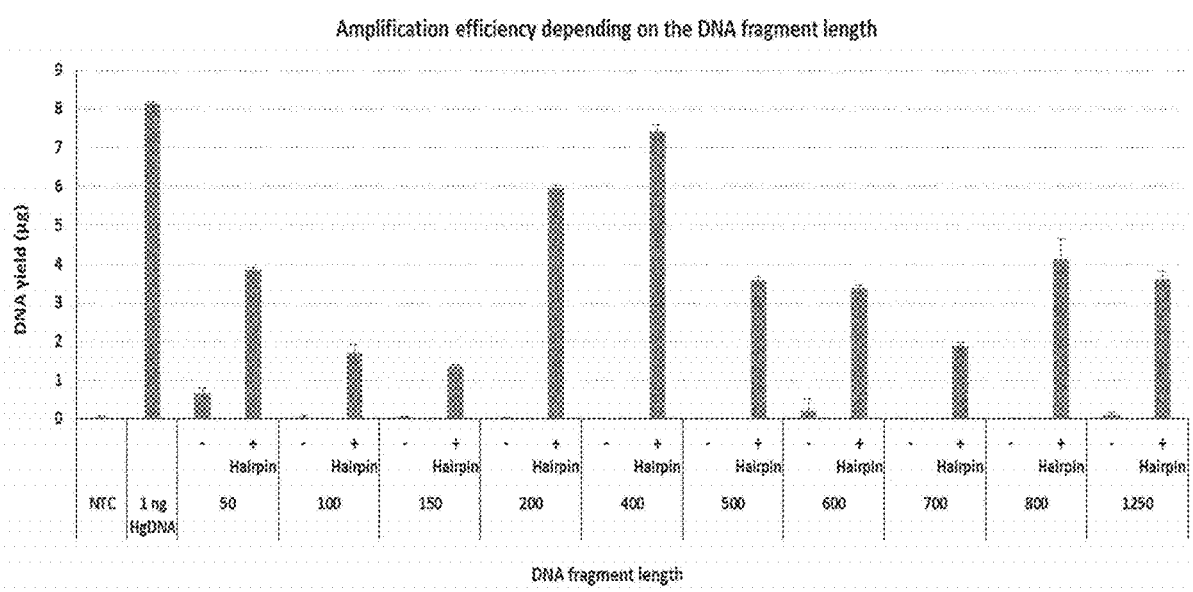
FIG. 6 shows the amplification yields of short DNA molecules (from 50 to 1250 bp), requiring the addition of hairpin adaptors, by primase-initiated multiple displacement amplification.

Hairpin Addition at Both DNA Ends According to the Disclosure Allows the Efficient Amplification of DNA Molecules from 50 bp up to 1250 bp by TruePrime Multiple Displacement Amplification Shown in FIG. 6 is the amplification of DNA molecules ranging from 50 bp up to 1250 bp (50, 100, 150, 200, 400, 500, 600, 700, 800 and 1250 bp) obtained by PCR amplification. The end-repair and dA-tailing reaction, and the addition of the hairpin adaptors enables the efficient amplification of the different DNA molecules by TruePrime.

Example 4

TthPrimPol DNA Primase Efficiency Depending on the Hairpin Sequence of the Adaptor Shown in FIG. 7 are the different hairpin adaptors tested. All the adaptors have self-complementary sequences that allow auto-hybridization of the molecules forming a hairpin. The hairpin sequence and length differ in each case.

Figure 8:
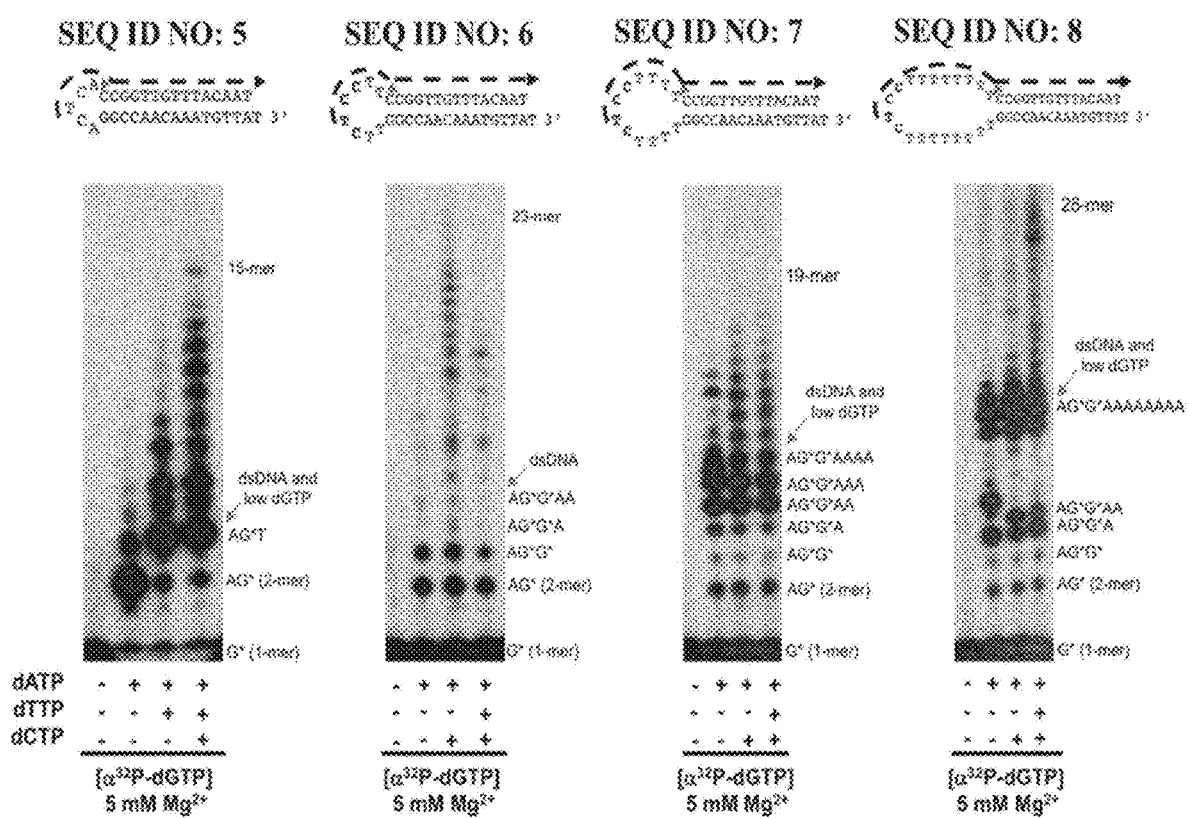
FIG. 8 shows TthPrimPol DNA primase activity observed in each hairpin adaptor.

Shown in FIG. 8 is the DNA primase activity of TthPrimPol, the enzyme in charge of synthesizing the DNA primers for Phi29 DNA pol in TruePrime, using adaptors with different hairpin sizes and sequences. Adaptor 1 shows the highest activity, as can be deduced from the amount of DNA primers generated, as well as the almost complete absence of the unincorporated labelled nucleotide (G*), which highlights the efficiency of the DNA primase activity using this molecule. Surprisingly, the other three adaptors that contain a more accessible TthPrimPol recognition sequence (3' CTCC 5')[46] show less activity, especially in the case of adaptor 2. Adaptor 1 shows the highest activity and the shortest sequence, so it becomes the best candidate to be used in the cfDNA amplification workflow.

Example 5

Present Method Results in a Very Efficient Amplification of Cell-Free DNA Samples from Cancer Patients 48 cancer patients were recruited for this study under informed consent. 10 mls of blood were extracted using Streck Cell-free DNA BCT® tubes. 3 mls pf plasma were immediately isolated through a double-spin centrifugation protocol to avoid genomic DNA contamination from nucleated blood cells. Cell-free DNA was purified from 1 ml of plasma samples using the gold-standard cfDNA purification kit (Qiagen QIAamp Circulating Nucleic Acid Kit). Different yields were obtained in each case quantified by Qubit (ranging from 0.12 up to 21.6 ng/µl). Cell-free DNA size profile was analyzed using the Bioanalyzer HS kit to confirm the presence of the apoptotic cell-free DNA molecules of interest (size ~160-170 bp) and the absence of other longer DNA molecules.

Figure 9:
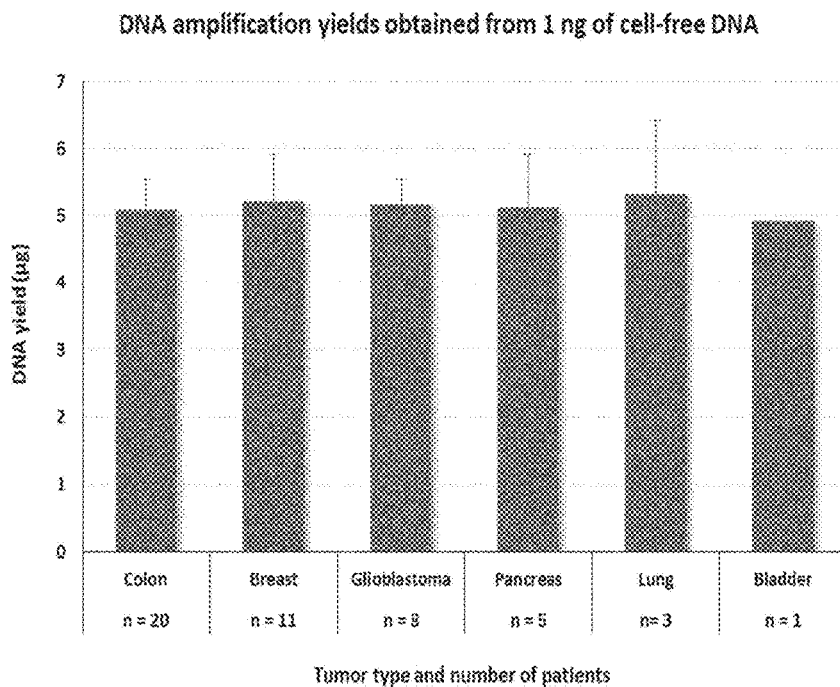
FIG. 9 shows DNA amplification yields obtained from cfDNA samples from 48 cancer patients, as well as the detailed protocol of the amplification process.

1 ng of cfDNA in each case followed the disclosure workflow for cfDNA amplification (steps shown in FIG. 9, left part); i.e. beginning with the steps of end-repair, dA-tailing and adaptor 1 ligation. After that, resulting samples (15 µl) were amplified using the TruePrime technology. Shown in FIG. 9 (right part) are the amplification yields obtained. All cell-free DNA samples were efficiently amplified.

Example 6

Figure 10:
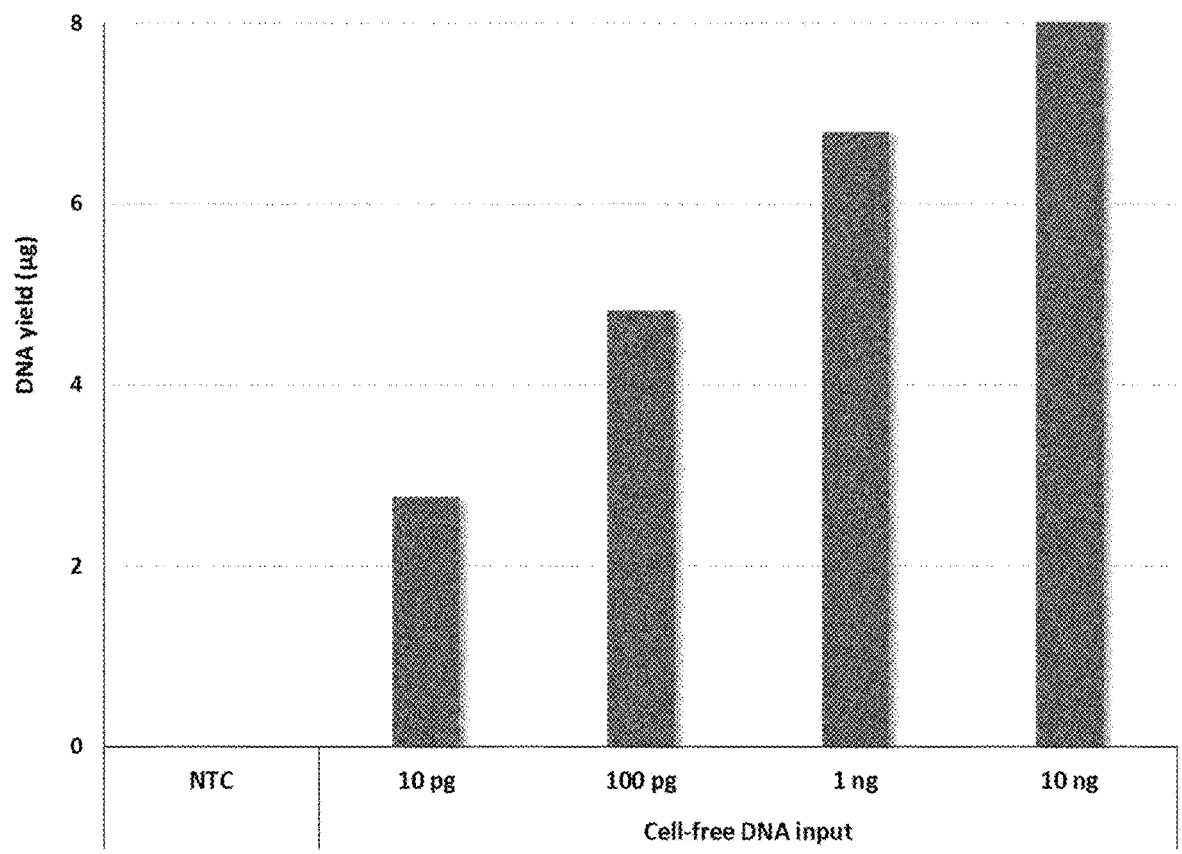
FIG. 10 shows the amplification yields in micrograms obtained from different amounts of cfDNA from a cancer patient.

Present Method Results in a Very Sensitive Amplification of Cell-Free DNA Samples from Cancer Patients Shown in FIG. 10 are the excellent sensitivity and efficiency of the disclosure workflow, which achieves DNA amplification yields in the range of micrograms starting from picograms of cell-free DNA. It is remarkable the proportionality between the input amount and the amplification yield observed.

Example 7

Short-Read (Illumina) and Long-Read (Oxford Nanopore MinION) Whole Genome Sequencing Confirms the Feasibility and Efficiency of the Method Workflow for the Amplification of Apoptotic Cell-Free DNA 4 ng of cell-free DNA from a colon cancer patient (T3N1aM0) were subjected to the disclosure workflow for cfDNA amplification in duplicate.

Long-read (Oxford Nanopore MinION) whole genome sequencing: 1500 ng of each amplified cell-free DNA were pre-treated with T7 endonuclease I before preparing the library to eliminate the multi-branched DNA structure. Ligation ID sequencing kit SQK-LSK108 was used and protocol ID genomic DNA sequencing for the MinION device using SQK-LSK 108 was followed. The flow cell was run for 48 hours.

The sequences from the Oxford Nanopore MinION run were analyzed and tested for the occurrence of the hairpin adaptor sequence [SEQ ID NO:1]. Although the sequencing quality was not high, the sequence of the hairpin adaptor [SEQ ID NO:1] could be found in almost every read and separated sequence fragments with a high similarity (proven by BLAST of those fragments, which had identical genetic region as hit).

Figure 11:
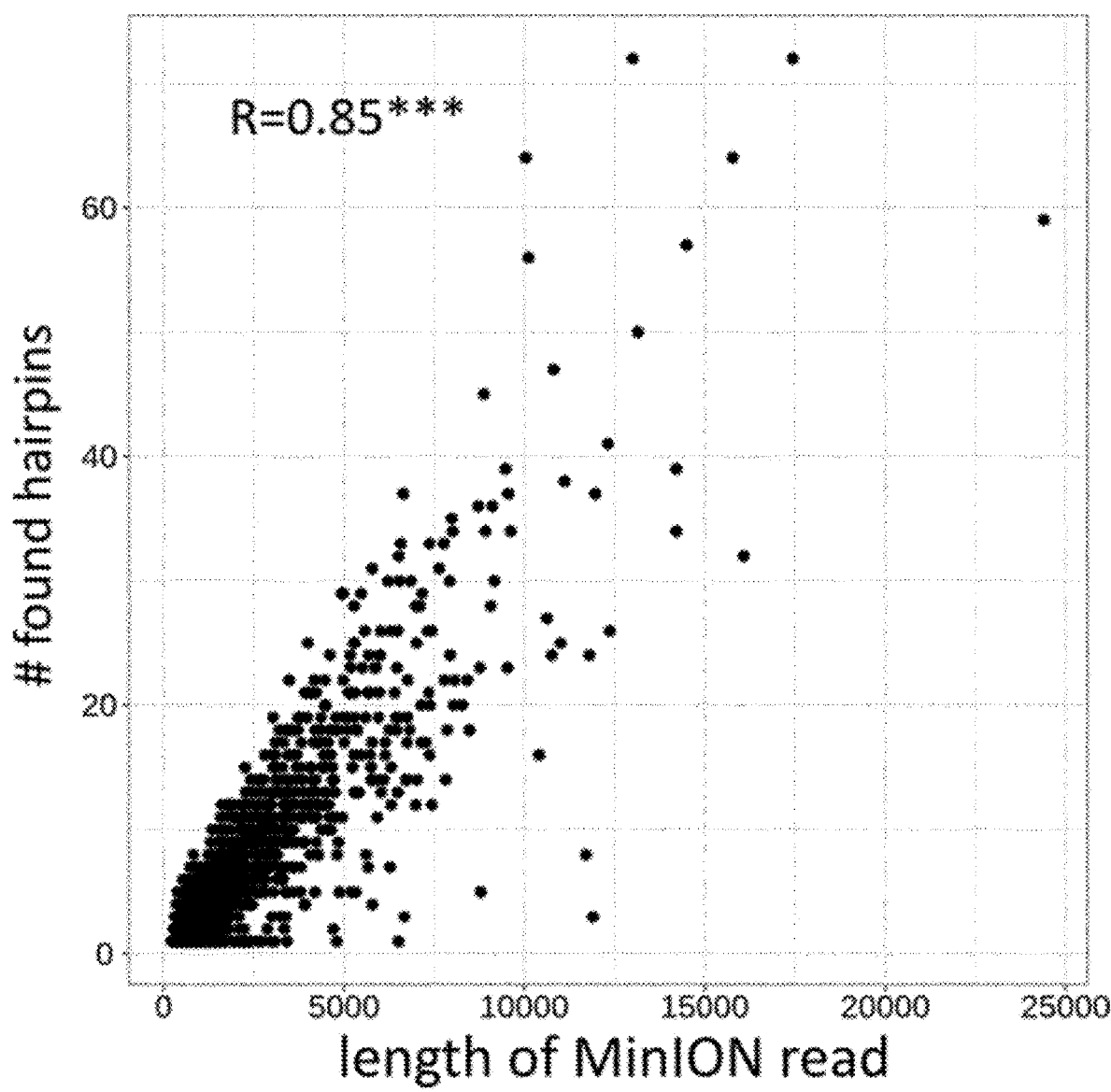
FIG. 11 shows the high correlation of fragments separated by the hairpin adaptor sequence [SEQ ID NO:1] in respect to the length of the MinION read (Oxford Nanopore).

Shown in FIG. 11 is the high correlation of fragments separated by the hairpin adaptor sequence [SEQ ID NO:1] in respect to the length of the MinION read.

Short-read (Illumina) whole genome sequencing: 1000 ng of each amplified cell-free DNA were sheared with Covaris to obtain 500 bp fragments. Sheared DNA was purified using AMPure beads and the library was prepared using the NxSeq AmpFREE Low DNA Library kit (Lucigen). Dual indices were added by PCR and the samples were sequenced in an Illumine HiSeq 2500 using paired-end reads (2×150 bp).

Figure 12:
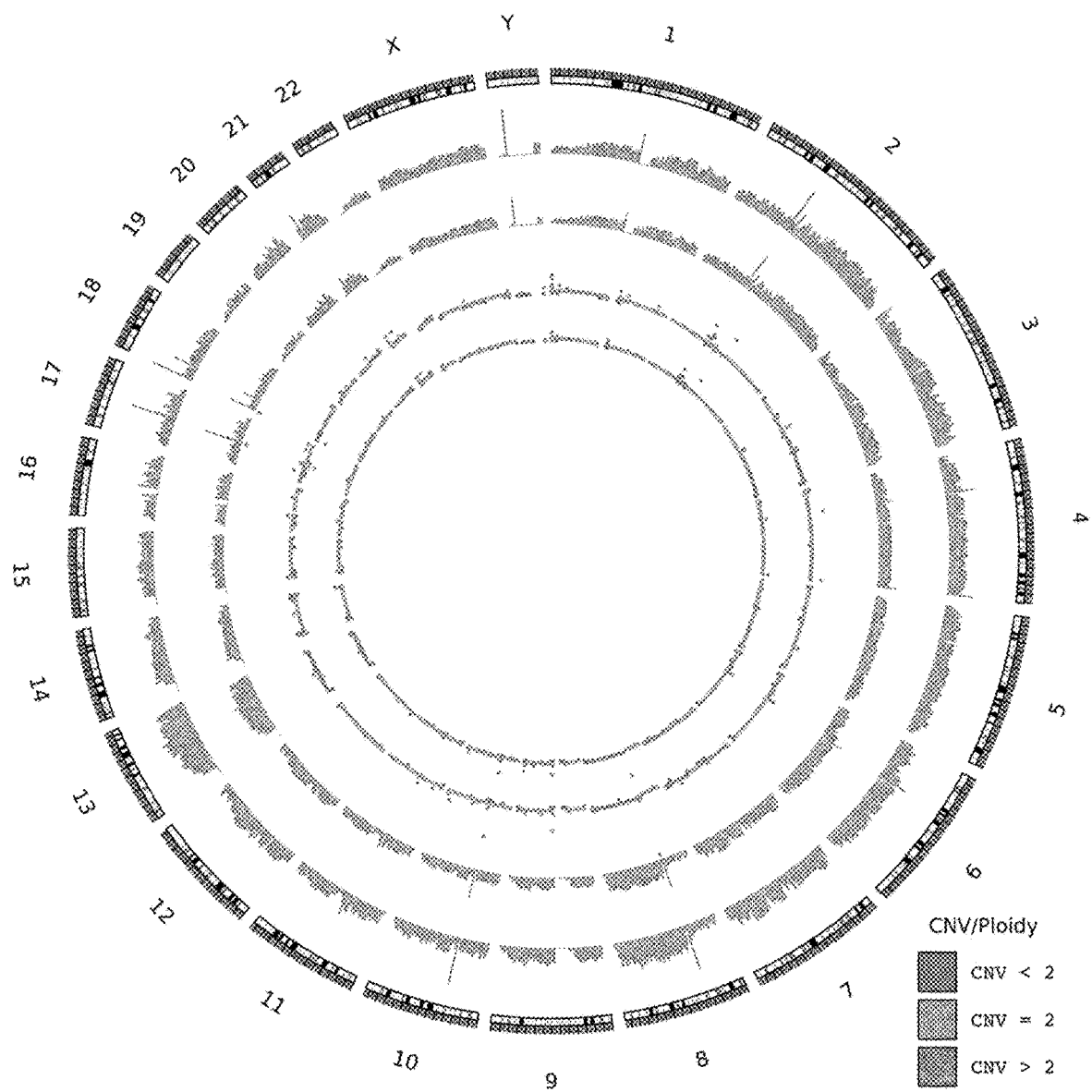
FIG. 12 shows the genome coverage and copy number variant detection from two amplified cfDNA samples from the same colon cancer patient.

Shown in FIG. 12 are the coverage and copy number variant (CNV) detection results. The coverage of two samples from the same patient looks nearly identical and highly even, as does the CNV plot, in which except for single parts both samples have an identical composition of ploidies. The reads were analyzed by CLC Genomics Workbench, combined into one read and then separated again at the position of the hairpin. The hairpin sequence could be found in almost all combined reads. The again separated and artificially created new paired reads were aligned to the human genome and analyzed for the coverage statistics, reproducibility and CNV content.

Figure 13:
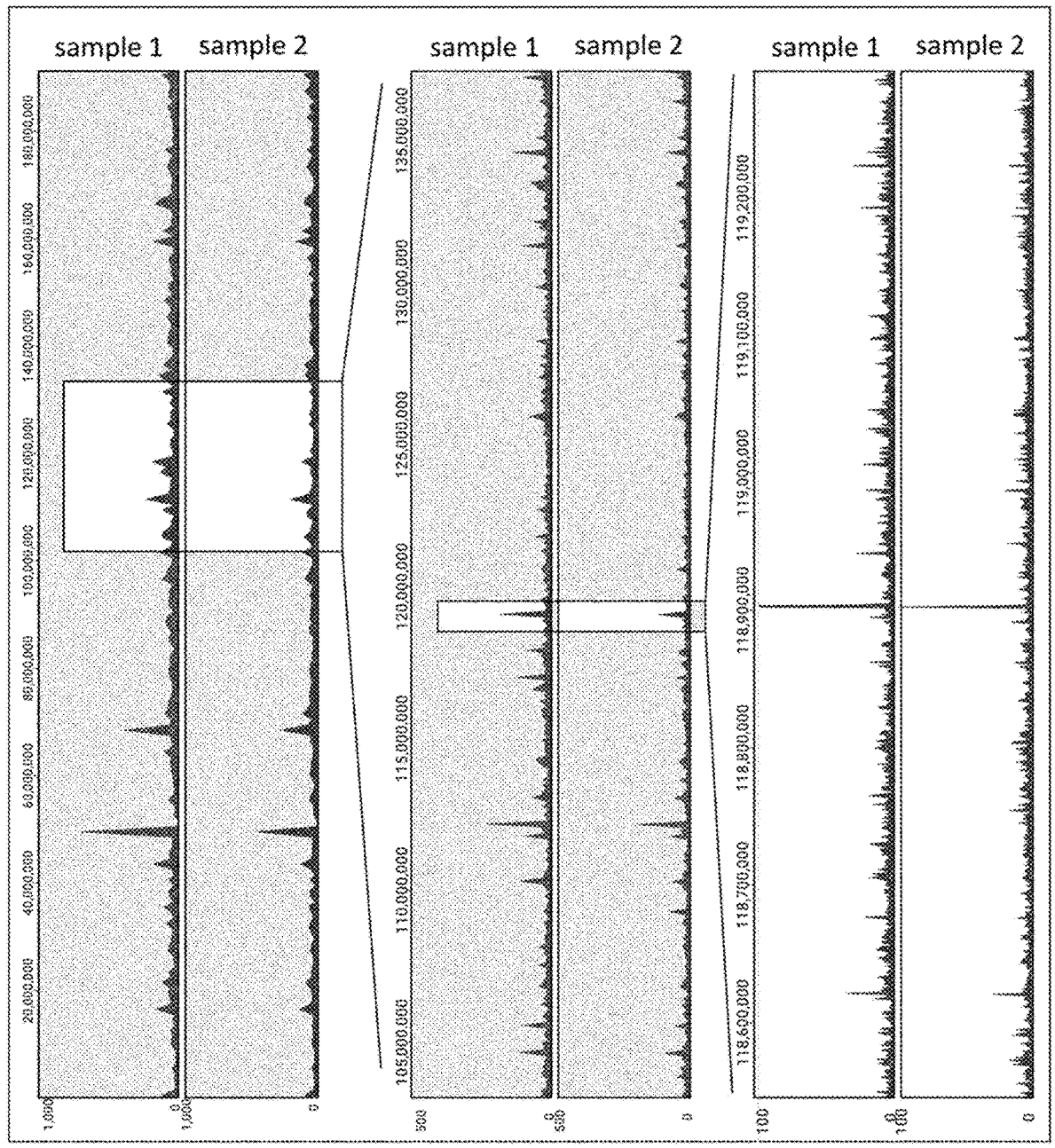
FIG. 13 shows the coverage plot from the two amplified cfDNA samples from the same colon cancer patient in different resolutions. This plot reflects the distribution of reads along chromosome 4 from two cfDNA samples from the same colon cancer patient amplified with the method described herein. Whole genome sequencing was carried out and the reads obtained were aligned to the human reference genome. A very even and homogeneous distribution of reads is observed in independent amplification reactions at different resolutions. The plot zooms in to show how similar the distribution pattern in both samples is.

Shown in FIG. 13 is the coverage plot from the two samples from one patient in different resolutions. It is remarkable the almost identical amplification and results from the post-sequencing process.

Example 8

Amplicon Sequencing Confirms the Feasibility and Efficiency of the Method Workflow for the Amplification of Apoptotic Cell-Free DNA 26.7, 84 and 150 ng of cell-free DNA from three different colon cancer patients (T3/4) were subjected to disclosure workflow for cfDNA amplification, obtaining 15, 17 and 20 µgs respectively. 20 ng of the non-amplified cfDNA and 50 ng of the amplified cfDNA from each patient were sequenced using the Oncomine™ Colon cfDNA Assay with tag molecular barcodes for multiplexing in an Ion Proton™ sequencing system, using an Ion Proton™ Chip. Libraries were prepared using the Ion Chef™ system. Read alignment was carried out using the Torrent Suite Software and the variant calling was performed using the CLC software with the following settings: Ploidy=2. Ignore positions with coverage above=1000000. Restrict calling to target regions=Oncomine_Colon_cfDNA.03062017.
Designed_BED. Ignore broken pairs=No. Ignore non-specific matches=Reads. Minimum coverage=10. Minimum count=2. Minimum frequency (%)=1.0–35.0. Base quality filter=No. Read direction filter=No. Relative read direction filter=No. Read position filter=No. Remove pyro-error variants=No. Create track=Yes. Create annotated table=No.

Figure 14:
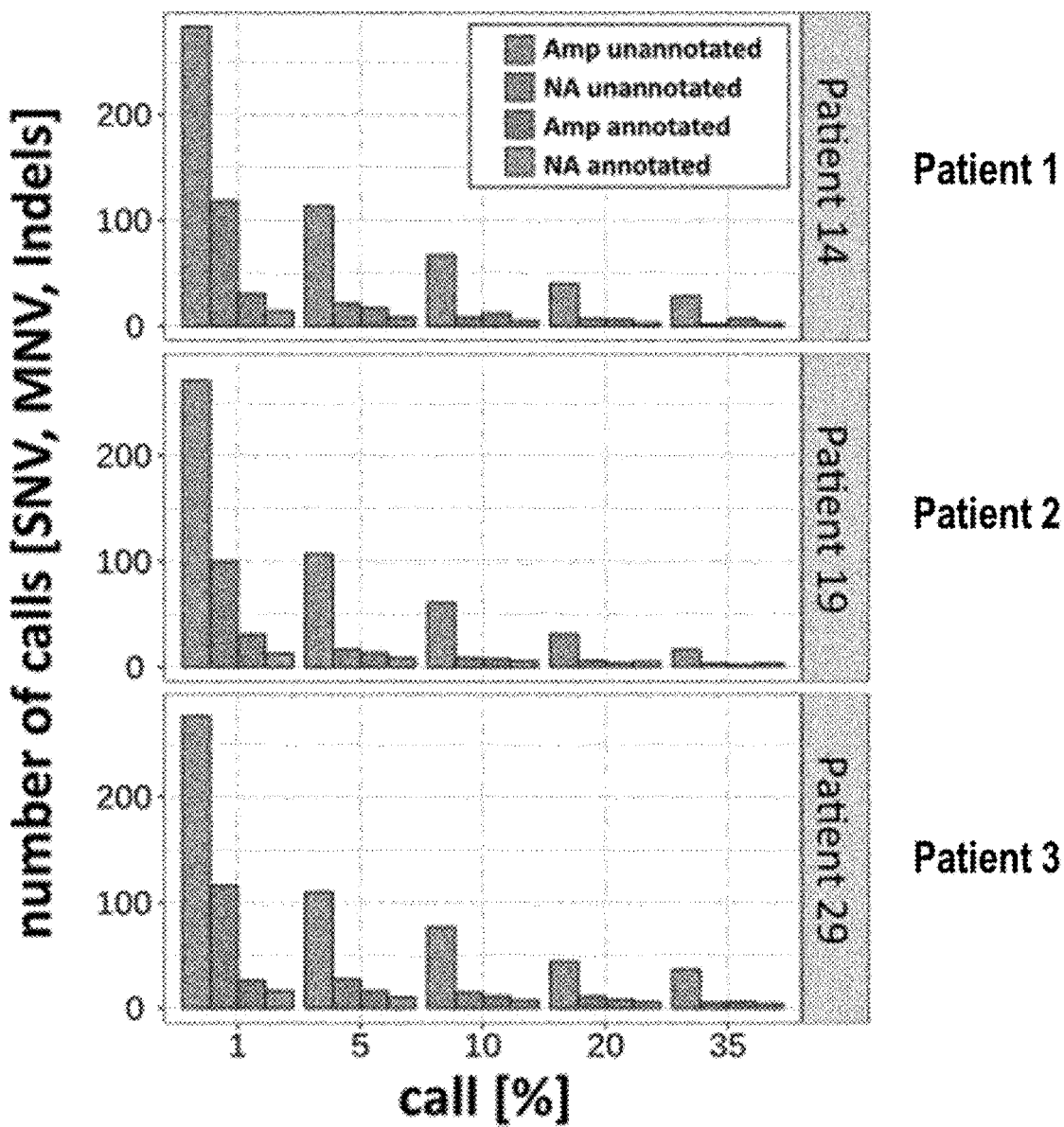
FIG. 14 shows the number of annotated and non-annotated variants detected in each of the three patients comparing the amplified and non-amplified cfDNA samples in each case.

Variant calling was carried out for single nucleotide variants, multiple nucleotide variants, insertions and deletions at different frequencies, from 35% to 1%. Shown in FIG. 14 are the number of annotated and non-annotated variants detected in each patient comparing the amplified and non-amplified cfDNA samples in each case.

In the three cases, more variants were detected in the amplified sample than in the non-amplified one, independently of the mutation allele frequency threshold. Additionally, the number of annotated variants is also higher in the amplified samples than in the non-amplified ones.

Figure 15:
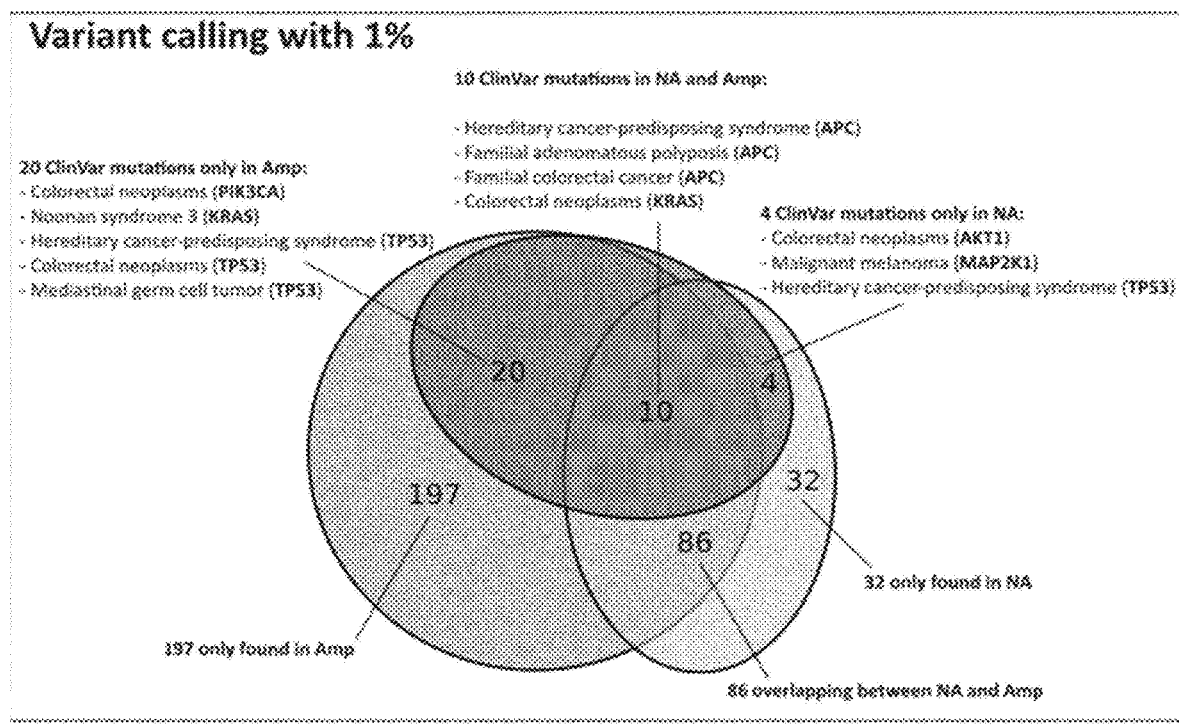
FIG. 15 shows the variant calling results obtained for the first patient at two different allele frequencies (1% and 35%) and the correlation between amplified and non-amplified cfDNA samples.
Figure 15:
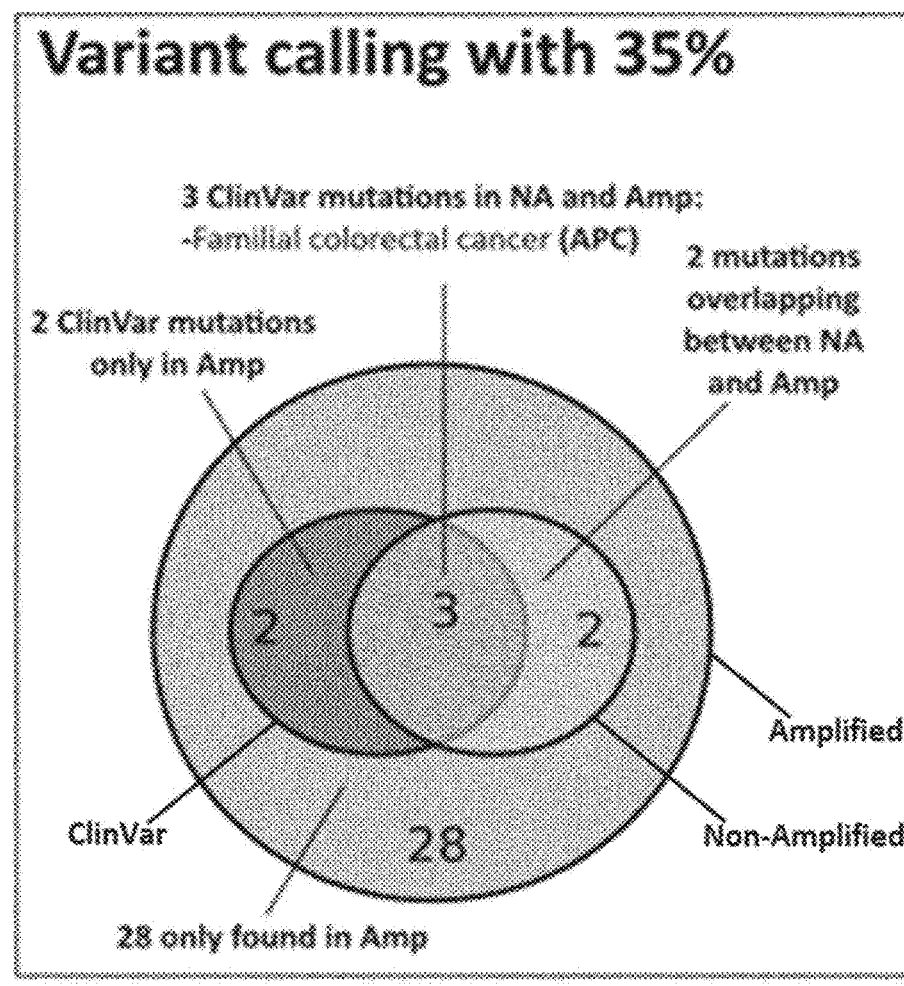

Shown in FIG. 15 are the results obtained for the first patient and the higher number of clinically relevant variants in the amplified sample in comparison to the non-amplified cfDNA sample from the same patient at two different allele frequencies (1% and 35%). For the 1% frequency, 30 clinically relevant (ClinVar) mutations are detected in the amplified sample, while only 14 in the non-amplified one. From those 14, 10 are also detected in the amplified sample. For the 35% frequency, 3 ClinVar mutations are detected in the non-amplified sample. Those 3 and 2 additional ClinVar mutations are found in the amplified material.

Figure 16:
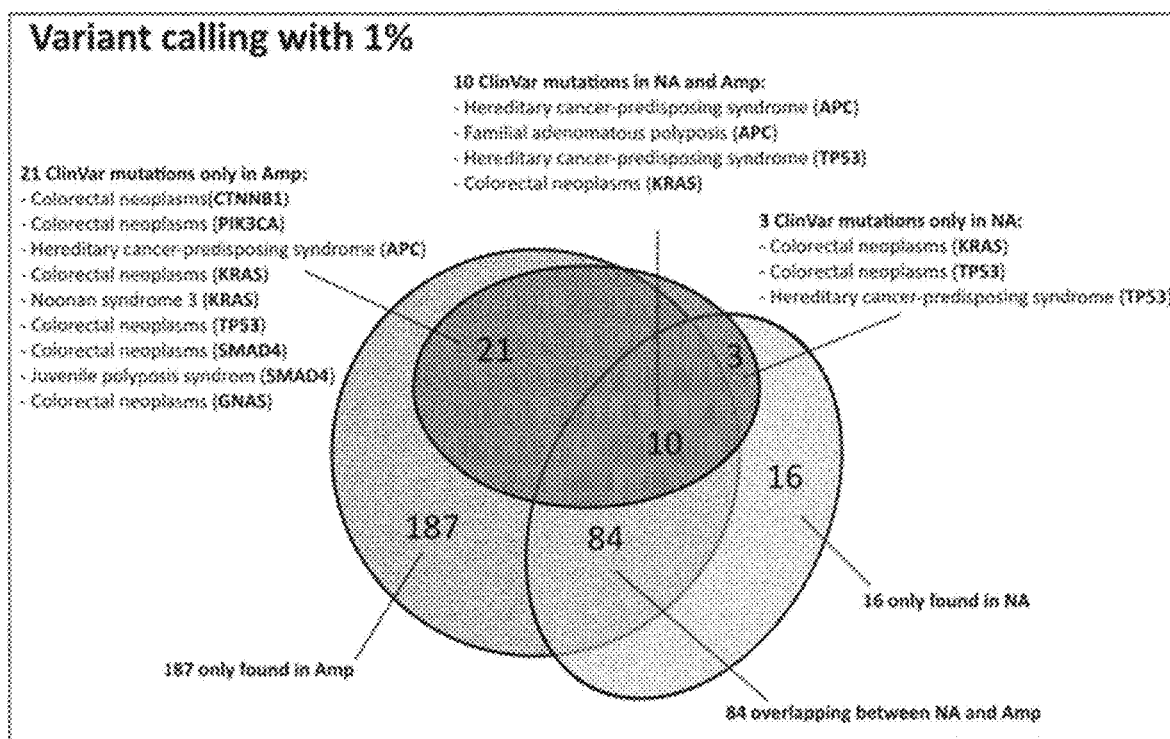
FIG. 16 shows the variant calling results obtained for the second patient at two different allele frequencies (1% and 35%) and the correlation between amplified and non-amplified cfDNA samples.
Figure 16:
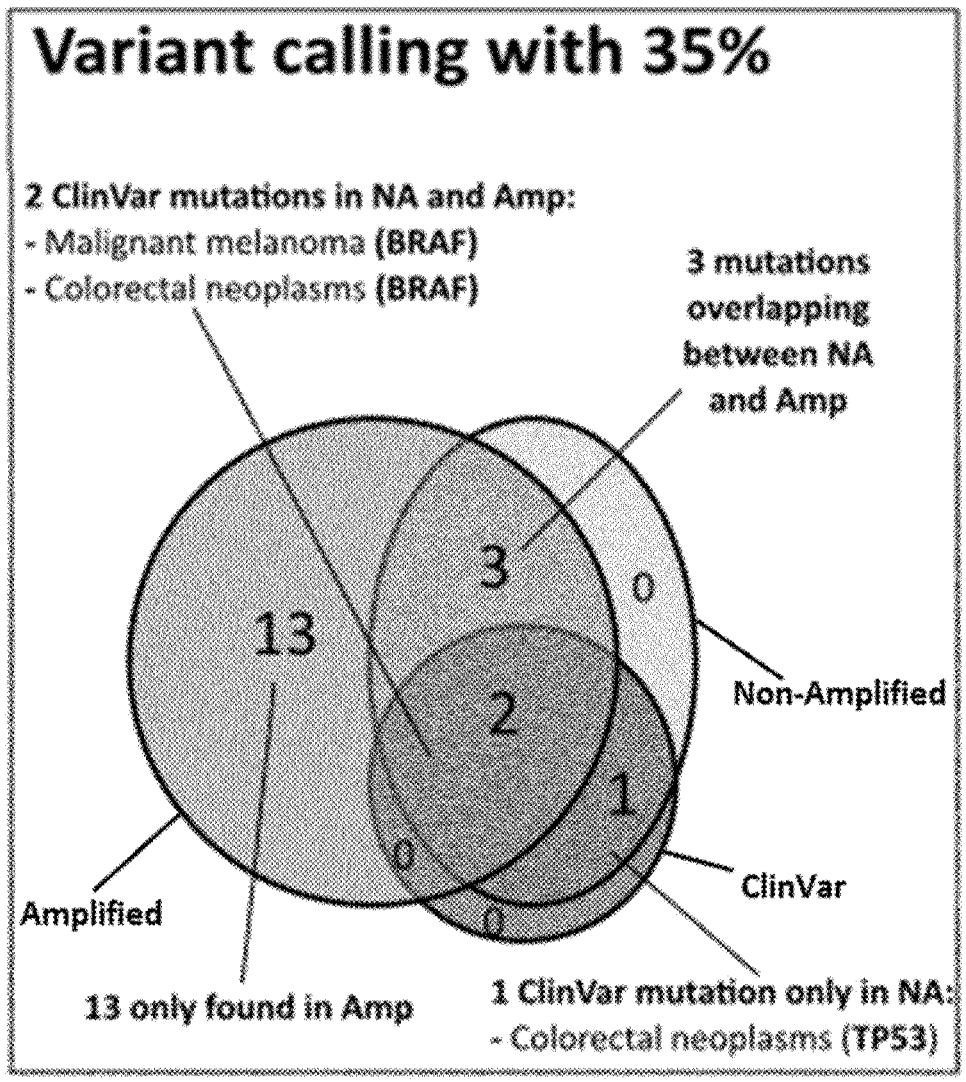

Shown in FIG. 16 are the results obtained for the second patient and the higher number of clinically relevant variants in the amplified sample in comparison to the non-amplified cfDNA sample from the same patient at two different allele frequencies (1% and 35%). For the 1% frequency, 31 ClinVar mutations are detected in the amplified sample, while only 13 in the non-amplified one. From those 13, 10 are also covered in the amplified sample.

Figure 17:
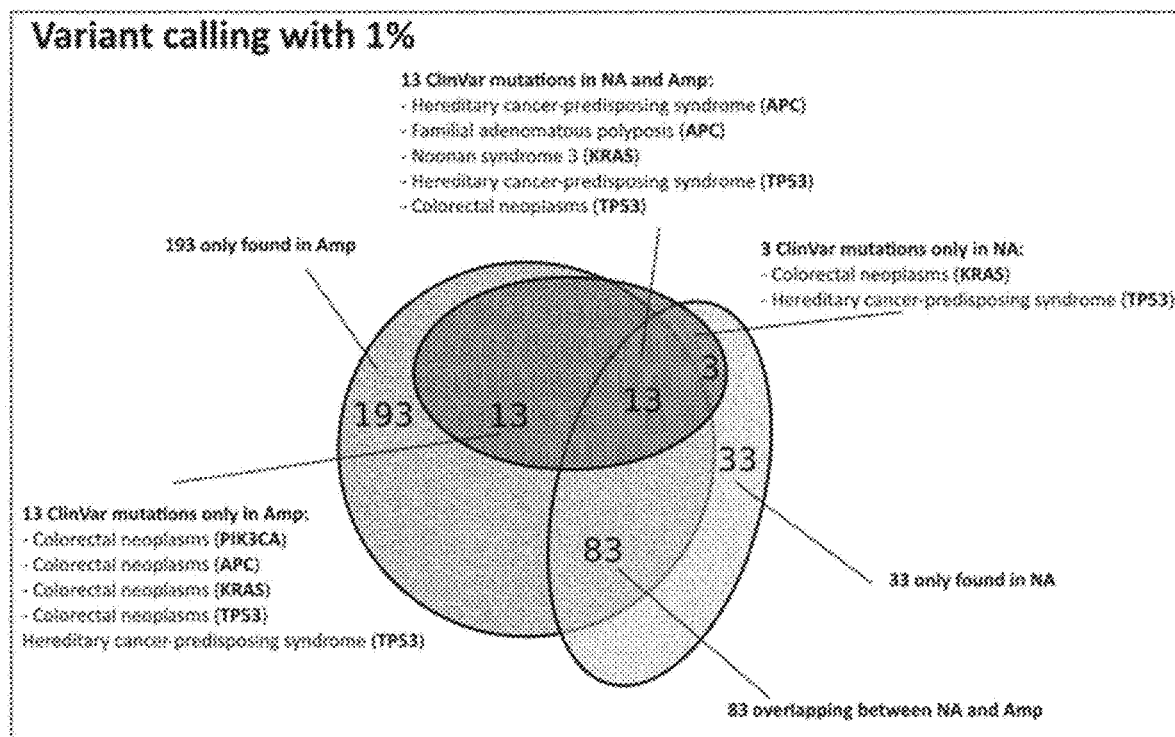
FIG. 17 shows the variant calling results obtained for the third patient at two different allele frequencies (1% and 35%) and the correlation between amplified and non-amplified cfDNA samples.
Figure 17:
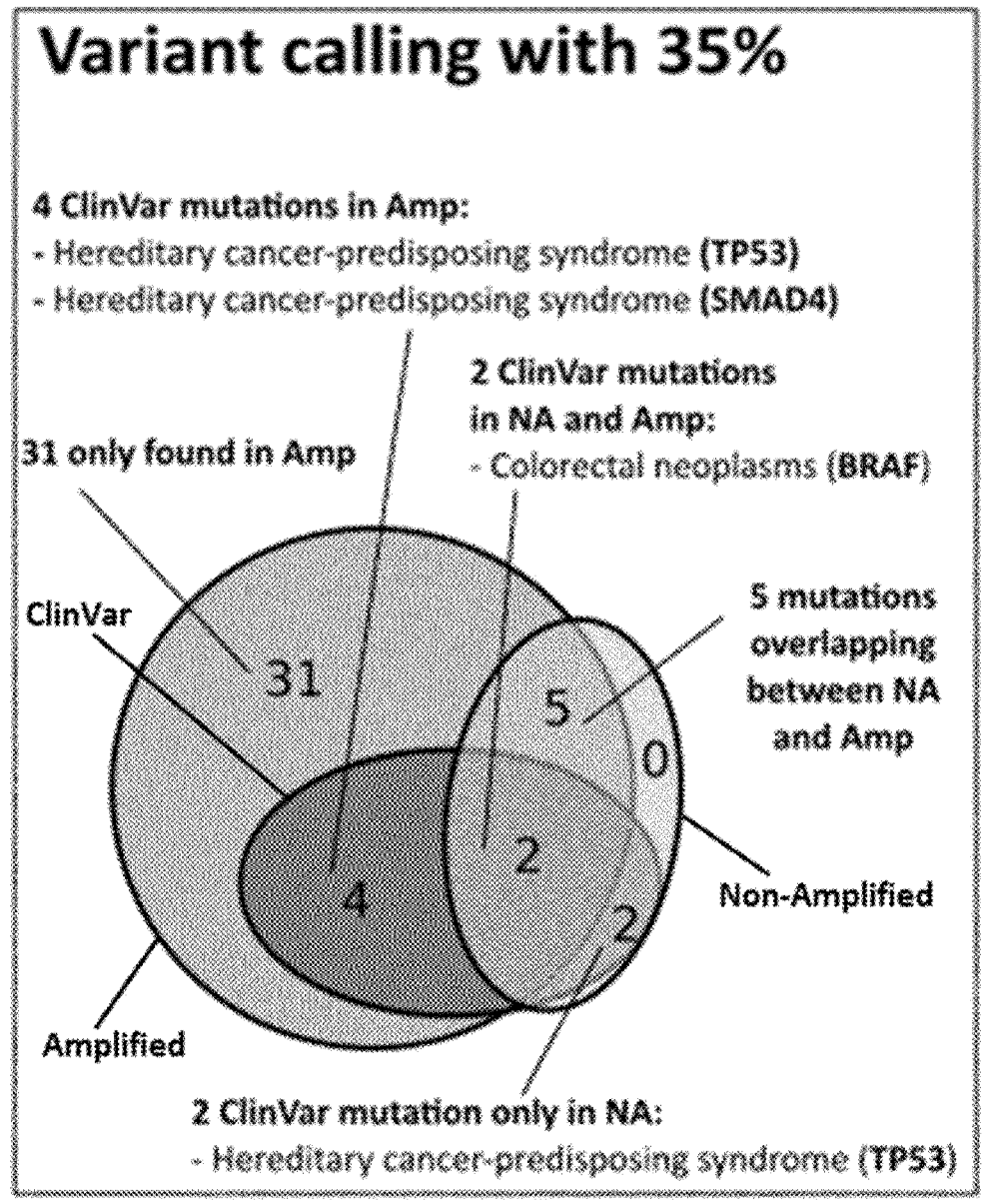

Shown in FIG. 17 are the results obtained for the third patient and the higher number of clinically relevant variants in the amplified sample in comparison to the non-amplified cfDNA sample from the same patient at two different allele frequencies (1% and 35%). For the 1% frequency, 26 ClinVar mutations are detected in the amplified sample, while only 16 in the non-amplified one. From those 16, 13 are also covered in the amplified sample.

Therefore, the use of the procedure of the disclosure before amplicon sequencing increases the sensitivity of the analysis, enabling the detection of more clinically relevant variants.

EXEMPLARY EMBODIMENTS

Exemplary embodiments of the invention include the following:

1. A method of amplifying DNA comprising: a) providing linear double stranded DNA molecules; b) attaching single-stranded adaptors to both ends of the linear double stranded DNA molecules to produce single stranded, covalently closed DNA molecules; and c) amplifying the single-stranded, covalently closed DNA molecules in a single operation by (i) rolling circle amplification and (ii) multiple displacement amplification.

2. The method of embodiment 1, wherein the linear double stranded DNA molecules comprise apoptotic cell free DNA molecules, e.g., having sizes less than 480 bp, less than 320 bp, or between about 140 bp and 180 bp (e.g., averaging about 160 bp).

3. The method of embodiment 1, wherein providing the linear double stranded DNA comprises fragmenting chromosomal DNA.

4. The method of any of the previous embodiments wherein the linear double stranded DNA is derived from one or more bodily fluids from mammals, e.g., selected from CSF, blood, plasma, serum, ascites, urine, saliva, tear drops, milk, semen and synovial fluid.

5. The method of any of the previous embodiments, wherein providing the linear double stranded DNA comprises isolating the linear double stranded DNA from other cellular components in a biological sample.

6. The method of any of the previous embodiments, wherein providing the linear double stranded DNA comprises end-repair and/or dA-tailing.

7. The method of embodiment 5, wherein end repair is performed using one or more of T4 polynucleotide kinase (PNK), T4 DNA polymerase Klenow fragment and T4 DNA polymerase large fragment.

8. The method of embodiment 5, comprising performing dA tailing using Taq polymerase.

9. The method of any of the previous embodiments, wherein the adaptors comprise single-stranded DNA molecules.

10. The method of any of the previous embodiments, wherein the adaptors have a hairpin structure.

11. The method of any of the previous embodiments, comprising attaching adaptors having the following sequence: 5'TAACATTTGTTGGCCACTCAGGCCAACAAATGTTAT3' [SEQ ID NO:1].

12. The method of any of the previous embodiments, wherein the adaptors comprise a primase/polymerase recognition sequence.

13. The method of any of the previous embodiments, wherein attaching the adaptors comprises blunt-end ligation or sticky-end ligation.

14. The method of any of the previous embodiments, comprising:
providing apoptotic cell free DNA molecules;
performing end repair and dA tailing of the cell free DNA molecules; and
ligating hairpin adaptors comprising a dT overhang to the end repaired, dA tailed cell free DNA molecules.

15. The method of any of the previous embodiments, wherein amplification is primed by a primase/polymerase.

16. The method of any of the previous embodiments, wherein amplification is primed by *Thermus thermophilus* primase/polymerase (TthPrimPol).

17. The method of any of the previous embodiments, wherein amplification is primed by a TthPrimPol having the sequence of SEQ ID NO: 10.

18. The method of any of the previous embodiments, wherein amplification is primed by human primase/polymerase (HsPrimPol).

19. The method of any of the previous embodiments, wherein amplification is primed with random synthetic primers (e.g., random sequences typically 3 to 8 nucleotides in length, such as hexamers).

20. The method of any of the previous embodiments wherein amplification comprises strand extension using a polymerase having strand displacement activity.

21. The method of any of the previous embodiments wherein amplification comprises strand extension using Phi29 polymerase.

22. The method of any of the previous embodiments wherein amplification comprises primase-initiated multiple displacement amplification.

23. The method of any of the previous embodiments comprising using a primase/polymerase to generate primers on the DNA and using a polymerase having strand displacement activity to extend the primers.

24. The method of embodiment 23, wherein the primase/polymerase comprises TthPrimPol and the polymerase comprises Phi29 polymerase.

25. The method of any of the previous embodiments further comprising: d) sequencing the amplified DNA.

26. The method of embodiment 25, wherein sequencing comprises fragmenting the amplified DNA and attaching to the fragmented DNA sequencing platform-specific adaptors.

27. The method of embodiment 25, wherein sequencing is performed on selected sequences (amplicons), exomes, transcriptome or whole genome.

28. The method of embodiment 25, further comprising: e) detecting one or a plurality of genetic variants in the sequenced, amplified DNA.

29. The method of any of the preceding embodiments, further comprising quantifying the amplified DNA.

30. A method of amplifying DNA comprising: a) providing linear double stranded DNA molecules; b) performing end-repair and dA tailing on the DNA molecules; c) ligating hairpin adaptors to the end-repaired dA-tailed DNA molecules to produce adaptor-tagged DNA molecules; and d) amplifying the adaptor-tagged DNA molecules by (i) rolling circle amplification and (ii) multiple displacement amplification ("MDA").

31. The method of embodiment 30, wherein amplification comprises random-primed MDA, using Phi29 DNA polymerase and random synthetic primers.

32. The method of embodiment 30, wherein amplification comprises priming with a primase/polymerase (e.g., TthPrimPol).

33. A method of amplifying DNA comprising: a) providing linear double stranded DNA molecules; b) attaching single-stranded adaptors to both ends of the linear double stranded DNA molecules to produce single stranded, covalently closed DNA molecules; and c) amplifying the single-stranded, covalently closed DNA molecules by any combination of a thermostable DNA polymerase, e.g., Taq polymerase, random or degenerate primers and an optional ligase.

34. The method of embodiment 33, wherein amplification comprises Degenerate oligonucleotide-primed PCR (DOP-PCR), linker-adaptor PCR (LA-PCR), Primer Extension Pre-amplification PCR (PEP-PCR-/I-PEP-PCR), and variations thereof).

35. A method of amplifying DNA comprising: a) providing linear double stranded DNA molecules; b) attaching single-stranded adaptors to both ends of the linear double stranded DNA molecules to produce single stranded, covalently closed DNA molecules; and c) amplifying the single-stranded, covalently closed DNA molecules using any combination of a thermostable DNA polymerase (e.g., Taq polymerase) and a highly processive strand-displacement DNA polymerase (e.g., Phi29 polymerase or Bacillus stearothermophilus (Bst) polymerase).

36. The method of embodiment 35, wherein amplification comprises multiple annealing and looping-based amplification cycles (MALBAC).

37. A kit comprising: (a) a primase/polymerase;
(b) a polymerase having strand displacement activity; (c) deoxyribonucleotide triphosphates and (d) a single stranded hairpin adaptor.

38. The kit of embodiment 37, wherein the primase/polymerase is TthPrimPol.

39. The kit of embodiment 37, wherein the polymerase is Phi29 DNA polymerase.

40. The kit of embodiment 37, wherein the single strand adaptor has the sequence: 5' TAACATTTGTTGGC-CACTCAGGCCAACAAATGTTAT 3' [SEQ ID NO: 1].

41. The kit of embodiment 37, wherein the kit further comprises: d) one, two or three elements selected from: (i) one or more enzymes for dsDNA end repair (e.g., T4 DNA polymerase, klenow fragment and/or Taq polymerase); (ii) one or more enzymes for DNA ligation; (iii) optionally, a reagent to increase DNA ligation efficiency; (iv) reaction buffer; and (v) a buffer for use with any of the aforementioned elements.

42. The kit of any of the preceding embodiments wherein the kit further comprises: (a) reagents for isolation of apoptotic cell free DNA.

43. A DNA library comprising a population of adapter tagged, single-stranded, covalently closed DNA molecules, wherein each DNA molecule comprises first, second, third and fourth regions, wherein the second and fourth regions are complementary to each other and the first and third regions are not complementary to each other.

44. The DNA library of embodiment 43, wherein, the first and third regions have identical sequences.

45. The DNA library of embodiment 43 or embodiment 44, wherein the second and fourth regions comprise a segment of genomic DNA, e.g., apoptotic cfDNA.

REFERENCES (INCORPORATED HEREIN BY REFERENCE)

1. www.cancer.gov-targeted-therapies. 2016. Available from: https://www.cancer.gov/about-cancer/treatment/types/targeted-therapies/targeted-therapies-fact-sheet
2. Crowley E, Di Nicolantonio F, Loupakis F, Bardelli A. Liquid biopsy: monitoring cancer-genetics in the blood. *Nat Rev Clin Oncol* 2013, 10(8): 472-484.
3. Speicher M R, Pantel K. Tumor signatures in the blood. *Nat Biotechnol* 2014, 32(5):441-443.
4. Schwarzenbach H, Hoon D S, Pantel K. Cell-free nucleic acids as biomarkers in cancer patients. *Nat Rev Cancer* 2011, 11(6): 426-437.
5. Enderle D, Spiel A, Coticchia C M, Berghoff E, Mueller R, Schlumpberger M, et al. Characterization of RNA from Exosomes and Other Extracellular Vesicles Isolated by a Novel Spin Column-Based Method. *PLoS One* 2015, 10(8): e0136133.
6. Jia S, Zocco D, Samuels M L, Chou M F, Chammas R, Skog J, et al. Emerging technologies in extracellular vesicle-based molecular diagnostics. *Expert Rev Mol Diagn* 2014, 14(3): 307-321.
7. Skog J, Wurdinger T, van Rijn S, Meijer D H, Gainche L, Sena-Esteves M, et al. Glioblastoma microvesicles transport RNA and proteins that promote tumour growth and provide diagnostic biomarkers. *Nat Cell Biol* 2008, 10(12): 1470-1476.
8. Norton M E, Jacobsson B, Swamy G K, Laurent L C, Ranzini A C, Brar H, et al. Cell-free DNA analysis for noninvasive examination of trisomy. *N Engl J Med* 2015, 372(17): 1589-1597.
9. Stokowski R, Wang E, White K, Batey A, Jacobsson B, Brar H, et al. Clinical performance of non-invasive prenatal testing (NIPT) using targeted cell-free DNA analysis in maternal plasma with microarrays or next generation sequencing (NGS) is consistent across multiple controlled clinical studies. *Prenat Diagn* 2015.
10. Wagner A J, Mitchell M E, Tomita-Mitchell A. Use of cell-free fetal DNA in maternal plasma for noninvasive prenatal screening. *Clin Perinatol* 2014, 41(4): 957-966.
11. Bianchi D W, Parker R L, Wentworth J, Madankumar R, Saffer C, Das A F, et al. DNA sequencing versus standard prenatal aneuploidy screening. *N Engl J Med* 2014, 370 (9): 799-808.
12. Cuckle H, Benn P, Pergament E. Cell-free DNA screening for fetal aneuploidy as a clinical service. *Clin Biochem* 2015, 48(15): 932-941.
13. Robinson C, van den Boom D, Bombard A T. Noninvasive prenatal detection of aneuploidy. *Clin Obstet Gynecol* 2014, 57(1): 210-225.
14. Syngelaki A, Pergament E, Homfray T, Akolekar R, Nicolaides K H. Replacing the combined test by cell-free DNA testing in screening for trisomies 21, 18 and 13: impact on the diagnosis of other chromosomal abnormalities. *Fetal Diagn Ther* 2014, 35(3): 174-184.
15. Wax J R, Chard R, Litton C, Pinette M G. Prenatal aneuploidy screening using cell-free DNA. *Am J Obstet Gynecol* 2015.
16. De Vlaminck I, Martin L, Kertesz M, Patel K, Kowarsky M, Strehl C, et al. Noninvasive monitoring of infection and rejection after lung transplantation. *Proc Natl Acad Sci USA* 2015.
17. De Vlaminck I, Valantine H A, Snyder T M, Strehl C, Cohen G, Luikart H, et al. Circulating cell-free DNA enables noninvasive diagnosis of heart transplant rejection. *Sci Transl Med* 2014, 6(241): 241ra277.
18. Gielis E M, Ledeganck K J, De Winter B Y, Del Favero J, Bosmans J L, Claas F H, et al. Cell-free DNA: An Upcoming Biomarker in Transplantation. *Am J Transplant* 2015, 15(10): 2541-2551.

19. Snyder T M, Khush K K, Valantine H A, Quake S R. Universal noninvasive detection of solid organ transplant rejection. *Proc Natl Acad Sci USA* 2011, 108(15): 6229-6234.
20. Beck J, Oellerich M, Schulz U, Schauerte V, Reinhard L, Fuchs U, et al. Donor-Derived Cell-free DNA Is a Novel Universal Biomarker for Allograft Rejection in Solid Organ Transplantation. *Transplant Proc* 2015, 47(8): 2400-2403.
21. Aarthy R, Mani S, Velusami S, Sundarsingh S, Rajkumar T. Role of Circulating Cell-free DNA in Cancers. *Mol Diagn Ther* 2015, 19(6): 339-350.
22. Diehl F, Schmidt K, Choti M A, Romans K, Goodman S, Li M, et al. Circulating mutant DNA to assess tumor dynamics. *Nat Med* 2008, 14(9): 985-990.
23. Siravegna G, Bardelli A. Genotyping cell-free tumor DNA in the blood to detect residual disease and drug resistance. *Genome Biol* 2014, 15(8): 449.
24. Siravegna G, Bardelli A. Blood circulating tumor DNA for non-invasive genotyping of colon cancer patients. *Mol Oncol* 2015.
25. Thierry A R, Mouliere F, El Messaoudi S, Mollevi C, Lopez-Crapez E, Rolet F, et al. Clinical validation of the detection of KRAS and BRAF mutations from circulating tumor DNA. *Nat Med* 2014, 20(4): 430-435.
26. Lippi G, Sanchis-Gomar F, Cervellin G. Cell-free DNA for diagnosing myocardial infarction: not ready for prime time. *Clin Chem Lab Med* 2015.
27. Bettegowda C, Sausen M, Leary R J, Kinde I, Wang Y, Agrawal N, et al. Detection of circulating tumor DNA in early- and late-stage human malignancies. *Sci Transl Med* 2014, 6(224): 224ra224.
28. Dawson S J, Tsui D W, Murtaza M, Biggs H, Rueda O M, Chin S F, et al. Analysis of circulating tumor DNA to monitor metastatic breast cancer. *N Engl J Med* 2013, 368(13): 1199-1209.
29. Lebofsky R, Decraene C, Bernard V, Kamal M, Blin A, Leroy Q, et al. Circulating tumor DNA as a non-invasive substitute to metastasis biopsy for tumor genotyping and personalized medicine in a prospective trial across all tumor types. *Mol Oncol* 2015, 9(4): 783-790.
30. Breitbach S, Tug S, Helmig S, Zahn D, Kubiak T, Michal M, et al. Direct quantification of cell-free, circulating DNA from unpurified plasma. *PLoS One* 2014, 9(3): e87838.
31. Li M, Diehl F, Dressman D, Vogelstein B, Kinzler K W. BEAMing up for detection and quantification of rare sequence variants. *Nat Methods* 2006, 3(2): 95-97.
32. Butler T M, Johnson-Camacho K, Peto M, Wang N J, Macey T A, Korkola J E, et al. Exome Sequencing of Cell-free DNA from Metastatic Cancer Patients Identifies Clinically Actionable Mutations Distinct from Primary Disease. *PLoS One* 2015, 10(8): e0136407.
33. Murtaza M, Dawson S J, Tsui D W, Gale D, Forshew T, Piskorz A M, et al. Non-invasive analysis of acquired resistance to cancer therapy by sequencing of plasma DNA. *Nature* 2013, 497(7447): 108-112.
34. Newman A M, Bratman S V, To J, Wynne J F, Eclov N C, Modlin L A, et al. An ultrasensitive method for quantitating circulating tumor DNA with broad patient coverage. *Nat Med* 2014, 20(5): 548-554.
35. De Mattos-Arruda L, Weigelt B, Cortes J, Won H H, Ng C K, Nuciforo P, et al. Capturing intra-tumor genetic heterogeneity by de novo mutation profiling of circulating cell-free tumor DNA: a proof-of-principle. *Ann Oncol* 2014, 25(9): 1729-1735.
36. Wang Y, Springer S, Zhang M, McMahon K W, Kinde I, Dobbyn L, et al. Detection of tumor-derived DNA in cerebrospinal fluid of patients with primary tumors of the brain and spinal cord. *Proc Natl Acad Sci USA* 2015, 112(31): 9704-9709.
37. Forshew T, Murtaza M, Parkinson C, Gale D, Tsui D W, Kaper F, et al. Noninvasive identification and monitoring of cancer mutations by targeted deep sequencing of plasma DNA. *Sci Transl Med* 2012, 4(136): 136ra168.
38. Kinde I, Papadopoulos N, Kinzler K W, Vogelstein B. FAST-SeqS: a simple and efficient method for the detection of aneuploidy by massively parallel sequencing. *PLoS One* 2012, 7(7): e41162.
39. Belic J, Koch M, Ulz P, Auer M, Gerhalter T, Mohan S, et al. Rapid Identification of Plasma DNA Samples with Increased ctDNA Levels by a Modified FAST-SeqS Approach. *Clin Chem* 2015, 61(6): 838-849.
40. Tie J, Kinde I, Wang Y, Wong H L, Roebert J, Christie M, et al. Circulating tumor DNA as an early marker of therapeutic response in patients with metastatic colorectal cancer. *Ann Oncol* 2015, 26(8): 1715-1722.
41. Diehl F, Li M, He Y, Kinzler K W, Vogelstein B, Dressman D. BEAMing: single-molecule PCR on microparticles in water-in-oil emulsions. *Nat Methods* 2006, 3(7): 551-559.
42. Dressman D, Yan H, Traverso G, Kinzler K W, Vogelstein B. Transforming single DNA molecules into fluorescent magnetic particles for detection and enumeration of genetic variations. *Proc Natl Acad Sci USA* 2003, 100(15): 8817-8822.
43. Li M, Chen W D, Papadopoulos N, Goodman S N, Bjerregaard N C, Laurberg S, et al. Sensitive digital quantification of DNA methylation in clinical samples. *Nat Biotechnol* 2009, 27(9): 858-863.
44. Tabernero J, Lenz H-J, Siena S, Sobrero A, Falcone A, Ychou M, et al. Analysis of circulating DNA and protein biomarkers to predict the clinical activity of regorafenib and assess prognosis in patients with metastatic colorectal cancer: a retrospective, exploratory analysis of the CORRECT trial. *The Lancet Oncology* 2015, 16(8): 937-948.
45. Diaz L A, Jr., Williams R T, Wu J, Kinde I, Hecht J R, Berlin J, et al. The molecular evolution of acquired resistance to targeted EGFR blockade in colorectal cancers. *Nature* 2012, 486(7404): 537-540.
46. Picher A J, Budeus B, Wafzig O, Kruger C, Garcia-Gómez S, Martinez-Jiménez MI, Diaz-Talavera A, Weber D, Blanco L & Schneider A. TruePrime is a novel method for whole-genome amplification from single cells based on TthPrimpol. *Nat Comm* 2016, Nov. 29; 7:13296
47. Kandoth C, McLellan M D, Vandin F, Ye K, Niu B, Lu C, et al. Mutational landscape and significance across 12 major cancer types. *Nature* 2013, 502(7471): 333-339.
48. Bamford S, Dawson E, Forbes S, Clements J, Pettett R, Dogan A, et al. The COSMIC (Catalogue of Somatic Mutations in Cancer) database and website. *Br J Cancer* 2004, 91(2): 355-358.
49. Forbes S A, Beare D, Gunasekaran P, Leung K, Bindal N, Boutselakis H, et al. COSMIC: exploring the world's knowledge of somatic mutations in human cancer. *Nucleic Acids Res* 2015, 43(Database issue): D805-811.
50. Adzhubei I A, Schmidt S, Peshkin L, Ramensky V E, Gerasimova A, Bork P, et al. A method and server for predicting damaging missense mutations. *Nat Methods* 2010, 7(4): 248-249.

51. Kumar P, Henikoff S, Ng P C. Predicting the effects of coding non-synonymous variants on protein function using the SIFT algorithm. *Nat Protoc* 2009, 4(7): 1073-1081.
52. Ng P C, Henikoff S. Predicting deleterious amino acid substitutions. *Genome Res* 2001, 11(5):863-874.
53. Ng P C, Henikoff S. SIFT: Predicting amino acid changes that affect protein function. *Nucleic Acids Res* 2003, 31(13): 3812-3814.
54. Sim N L, Kumar P, Hu J, Henikoff S, Schneider G, Ng P C. SIFT web server: predicting effects of amino acid substitutions on proteins. *Nucleic Acids Res* 2012, 40(Web Server issue): W452-457.
55. WO 2014/140309, "Methods for amplification and sequencing using thermostable TthPrimpol", Sep. 14, 2018.
56. WO 2011/047307A1, "Multiple Displacement Amplification", Apr. 21, 2011.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3".

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

What is claimed is:

1. A method of amplifying DNA comprising:
    a) providing linear double-stranded DNA molecules;
    b) attaching single-stranded adaptors comprising a non-complementary region of fewer than 25 nucleotides and comprising an XTC priming sequence, wherein X is A, C, G or T, to both ends of the linear double-stranded DNA molecules to produce single-stranded, covalently closed DNA molecules; and
    c) amplifying the single-stranded, covalently closed DNA molecules in a single operation by (i) rolling circle amplification and (ii) multiple displacement amplification.

2. The method of claim 1, wherein the linear double-stranded DNA molecules comprise apoptotic cell-free DNA molecules.

3. The method of claim 1, wherein the linear double-stranded DNA is derived from one or more bodily fluids from mammals.

4. The method of claim 1, wherein providing the linear double-stranded DNA comprises end-repair and/or dA-tailing.

5. The method of claim 1, wherein the adaptors have a hairpin structure.

6. The method of claim 1, comprising attaching adaptors having the following sequence: 5'TAACATTTGTTGGC-CACTCAGGCCAACAAATGTTAT3' [SEQ ID NO:1].

7. The method of claim 1, comprising:
    providing apoptotic cell-free DNA molecules;
    performing end repair and dA tailing of the cell-free DNA molecules; and
    ligating hairpin adaptors comprising a dT overhang to the end repaired, dA tailed cell-free DNA molecules.

8. The method of claim 1, wherein amplification is primed by a primase/polymerase.

9. The method of claim 1, wherein amplification is primed by *Thermus thermophilus* primase/polymerase (TthPrimPol).

10. The method of claim 1, wherein amplification comprises strand extension using a polymerase having strand displacement activity.

11. The method of claim 1, wherein amplification comprises primase-initiated multiple displacement amplification.

12. The method of claim 1, comprising using a primase/polymerase to generate primers on the DNA and using a polymerase having strand displacement activity to extend the primers.

13. The method of claim 12, wherein the primase/polymerase comprises TthPrimPol and the polymerase comprises Phi29 polymerase.

14. The method of claim 1, further comprising:
   d) sequencing the amplified DNA.

15. The method of claim 14, further comprising:
   e) detecting one or a plurality of genetic variants in the sequenced, amplified DNA.

16. The method of claim 2, wherein the apoptotic cell-free DNA molecules have a length between about 140 bp and 180 bp.

17. The method of claim 3, wherein the bodily fluids comprise one or more of CSF, blood, plasma, serum, ascites, urine, saliva, tear drops, milk, semen and synovial fluid.

18. The method of claim 1, wherein the XTC priming sequence is located in the loop portion of the adapter.

19. The method of claim 1, wherein amplification is primed by human primase/polymerase (HsPrimPol).

* * * * *

SEQUENCE LISTING

```
<160> NUMBER OF SEQ ID NOS: 10

<210> SEQ ID NO 1
<211> LENGTH: 36
<212> TYPE: DNA
<213> ORGANISM: artificial
<220> FEATURE:
<223> OTHER INFORMATION: Adaptor 1

<400> SEQUENCE: 1
taacatttgt tggccactca ggccaacaaa tgttat                                 36

<210> SEQ ID NO 2
<211> LENGTH: 39
<212> TYPE: DNA
<213> ORGANISM: Artificial
<220> FEATURE:
<223> OTHER INFORMATION: Adaptor 2

<400> SEQUENCE: 2
taacatttgt tggccttcct cttggccaac aaatgttat                              39

<210> SEQ ID NO 3
<211> LENGTH: 43
<212> TYPE: DNA
<213> ORGANISM: Artificial
<220> FEATURE:
<223> OTHER INFORMATION: Adaptor 3

<400> SEQUENCE: 3
taacatttgt tggccttttc ctcttttggc caacaaatgt tat                         43

<210> SEQ ID NO 4
<211> LENGTH: 51
<212> TYPE: DNA
```

-continued

```
<213> ORGANISM: Artificial
<220> FEATURE:
<223> OTHER INFORMATION: Adaptor 4

<400> SEQUENCE: 4
taacatttgt tggccttttt tttcctctttt tttttggcca acaaatgtta t        51

<210> SEQ ID NO 5
<211> LENGTH: 36
<212> TYPE: DNA
<213> ORGANISM: Artificial
<220> FEATURE:
<223> OTHER INFORMATION: Adaptor 5

<400> SEQUENCE: 5
taacatttgt tggccactca ggccaacaaa tgttat                          36

<210> SEQ ID NO 6
<211> LENGTH: 39
<212> TYPE: DNA
<213> ORGANISM: Artificial
<220> FEATURE:
<223> OTHER INFORMATION: Adaptor 6

<400> SEQUENCE: 6
taacatttgt tggccttcct cttggccaac aaatgttat                       39

<210> SEQ ID NO 7
<211> LENGTH: 43
<212> TYPE: DNA
<213> ORGANISM: Artificial
<220> FEATURE:
<223> OTHER INFORMATION: Adaptor 7

<400> SEQUENCE: 7
taacatttgt tggcctttc ctcttttggc caacaaatgt tat                   43

<210> SEQ ID NO 8
<211> LENGTH: 51
<212> TYPE: DNA
<213> ORGANISM: Artificial
<220> FEATURE:
<223> OTHER INFORMATION: Adaptor 8

<400> SEQUENCE: 8
taacatttgt tggccttttt tttcctctttt tttttggcca acaaatgtta t        51

<210> SEQ ID NO 9
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (10)..(15)
<223> OTHER INFORMATION: n is a, c, g, or t

<400> SEQUENCE: 9
cgactcgagn nnnnatgtg g                                           21

<210> SEQ ID NO 10
<211> LENGTH: 293
<212> TYPE: PRT
<213> ORGANISM: Thermus thermophilus

<400> SEQUENCE: 10
```

```
Met Arg Pro Ile Glu His Ala Leu Ser Tyr Ala Ala Gln Gly Tyr Gly
1               5                   10                  15

Val Leu Pro Leu Arg Pro Gly Gly Lys Glu Pro Leu Gly Lys Leu Val
                20                  25                  30

Pro His Gly Leu Lys Asn Ala Ser Arg Asp Pro Ala Thr Leu Glu Ala
            35                  40                  45

Trp Trp Arg Ser Cys Pro Arg Cys Gly Val Gly Ile Leu Pro Gly Pro
        50                  55                  60

Glu Val Leu Val Leu Asp Phe Asp Asp Pro Glu Ala Trp Glu Gly Leu
65                      70                  75                  80

Arg Gln Glu His Pro Ala Leu Glu Ala Ala Pro Arg Gln Arg Thr Pro
                85                  90                  95

Lys Gly Gly Arg His Val Phe Leu Arg Leu Pro Glu Gly Val Arg Leu
                100                 105                 110

Ser Ala Ser Val Arg Ala Ile Pro Gly Val Asp Leu Arg Gly Met Gly
            115                 120                 125

Arg Ala Tyr Val Val Ala Ala Pro Thr Arg Leu Lys Asp Gly Arg Thr
        130                 135                 140

Tyr Thr Trp Glu Ala Pro Leu Thr Pro Pro Glu Glu Leu Pro Pro Val
145                     150                 155                 160

Pro Gln Ala Leu Leu Leu Lys Leu Leu Pro Pro Pro Pro Pro Pro Arg
                165                 170                 175

Pro Ser Trp Gly Ala Val Gly Thr Ala Ser Pro Lys Arg Leu Gln Ala
            180                 185                 190

Leu Leu Gln Ala Tyr Ala Ala Gln Val Ala Arg Thr Pro Glu Gly Gln
        195                 200                 205

Arg His Leu Thr Leu Ile Arg Tyr Ala Val Ala Ala Gly Gly Leu Ile
    210                 215                 220

Pro His Gly Leu Asp Pro Arg Glu Ala Glu Glu Val Leu Val Ala Ala
225                 230                 235                 240

Ala Met Ser Ala Gly Leu Pro Glu Trp Glu Ala Arg Asp Ala Val Arg
                245                 250                 255

Trp Gly Leu Gly Val Gly Ala Ser Arg Pro Leu Val Leu Glu Ser Ser
            260                 265                 270

Ser Lys Pro Pro Glu Pro Arg Thr Tyr Arg Ala Arg Val Tyr Ala Arg
            275                 280                 285

Met Arg Arg Trp Val
        290
```